(12) United States Patent
Hess et al.

(10) Patent No.: US 9,863,243 B1
(45) Date of Patent: Jan. 9, 2018

(54) RUGGEDIZED DOWNHOLE TOOL FOR REAL-TIME MEASUREMENTS AND USES THEREOF

(71) Applicant: Sandia Corporation, Albuquerque, NM (US)

(72) Inventors: Ryan Falcone Hess, Sandia Park, NM (US); Scott C. Lindblom, Sandia Park, NM (US); William G. Yelton, Sandia Park, NM (US); Steven J. Limmer, Cleveland, OH (US); Timothy J. Boyle, Albuquerque, NM (US); Grzegorz Cieslewski, Sandia Park, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 217 days.

(21) Appl. No.: 14/698,773

(22) Filed: Apr. 28, 2015

(51) Int. Cl.
   *E21B 49/00* (2006.01)
   *H01R 43/20* (2006.01)
   (Continued)

(52) U.S. Cl.
   CPC .......... *E21B 49/008* (2013.01); *E21B 47/12* (2013.01); *G01N 27/333* (2013.01); *G01N 27/406* (2013.01); *H01R 43/20* (2013.01)

(58) Field of Classification Search
   CPC .. E21B 49/008; E21B 47/0002; E21B 47/011; E21B 47/12; G01N 27/333;
   (Continued)

(56) References Cited

U.S. PATENT DOCUMENTS

| | | |
|---|---|---|
| 3,793,608 A | 2/1974 | Ring et al. |
| 3,898,731 A | 8/1975 | Ring et al. |

(Continued)

FOREIGN PATENT DOCUMENTS

| | | |
|---|---|---|
| DE | 36 00 660 C1 | 1/1987 |
| WO | WO 2013/032859 A1 | 3/2013 |
| WO | WO 2013/039435 A1 | 3/2013 |

OTHER PUBLICATIONS

Hess, et al., "Development of a downhole tracer and pH measurement instrument for application in geothermal wells: Toward real-time chemical well logging," for American Chemical Society Fall 2013 Meeting, Report No. SAND2013-7430C 471106, published on Sep. 1, 2013, 20 pg.*

(Continued)

*Primary Examiner* — J. Christopher Ball
(74) *Attorney, Agent, or Firm* — Helen S. Baca

(57) ABSTRACT

The present invention relates to ruggedized downhole tools and sensors, as well as uses thereof. In particular, these tools can operate under extreme conditions and, therefore, allow for real-time measurements in geothermal reservoirs or other potentially harsh environments. One exemplary sensor includes a ruggedized ion selective electrode (ISE) for detecting tracer concentrations in real-time. In one embodiment, the ISE includes a solid, non-conductive potting material and an ion selective material, which are disposed in a temperature-resistant electrode body. Other electrode configurations, tools, and methods are also described.

20 Claims, 24 Drawing Sheets

(51) Int. Cl.
*G01N 27/333* (2006.01)
*G01N 27/406* (2006.01)
*E21B 47/12* (2012.01)

(58) Field of Classification Search
CPC ... G01N 27/406; H01L 23/3157; H01L 21/86; H01L 27/12; H01L 2924/13091; H01L 2924/3011; H01L 2224/32225; H01L 2224/73253; H01L 2224/73204; H01L 2224/16225; B81B 2207/115; H01R 43/20

See application file for complete search history.

(56) References Cited

U.S. PATENT DOCUMENTS

| | | | |
|---|---|---|---|
| 4,021,325 | A | 5/1977 | Pungor et al. |
| 4,077,261 | A | 3/1978 | Ring et al. |
| 4,264,424 | A | 4/1981 | Niedrach |
| 4,406,766 | A | 9/1983 | Macdonald |
| 4,575,410 | A | 3/1986 | Neti |
| 4,931,172 | A | 6/1990 | Kobos et al. |
| 5,630,994 | A | 5/1997 | Boyle et al. |
| 5,683,614 | A | 11/1997 | Boyle |
| 5,858,323 | A | 1/1999 | Boyle |
| 5,858,451 | A | 1/1999 | Boyle |
| 6,003,620 | A | 12/1999 | Sharma et al. |
| 6,086,957 | A | 7/2000 | Boyle et al. |
| 6,125,934 | A | 10/2000 | Lenn et al. |
| 6,153,317 | A | 11/2000 | Boyle et al. |
| 6,307,078 | B1 | 10/2001 | Boyle |
| 6,414,174 | B1 | 7/2002 | Boyle |
| 6,929,675 | B1 | 8/2005 | Bunge et al. |
| 7,030,355 | B1 | 4/2006 | Bochenski et al. |
| 7,189,428 | B1 | 3/2007 | Boyle |
| 7,256,290 | B1 | 8/2007 | Boyle |
| 7,301,223 | B2* | 11/2007 | Rodney ............... E21B 47/0002 257/629 |
| 7,591,871 | B1 | 9/2009 | Gerung et al. |
| 7,625,469 | B1 | 12/2009 | Yelton et al. |
| 7,741,486 | B1 | 6/2010 | Boyle |
| 7,896,071 | B2 | 3/2011 | Hinds et al. |
| 8,118,094 | B2 | 2/2012 | Mouget et al. |
| 8,296,078 | B1 | 10/2012 | Pfeifer et al. |
| 8,596,862 | B1 | 12/2013 | Pfeifer et al. |
| 8,962,512 | B1 | 2/2015 | Burton et al. |
| 9,209,766 | B1 | 12/2015 | Lindblom et al. |
| 9,463,532 | B2 | 10/2016 | Boyle et al. |
| 2005/0109098 | A1 | 5/2005 | DiFoggio |
| 2009/0050476 | A1 | 2/2009 | Zhang et al. |
| 2010/0044036 | A1 | 2/2010 | Mouget et al. |
| 2011/0215234 | A1 | 9/2011 | Rose |
| 2011/0265584 | A1 | 11/2011 | Segura et al. |
| 2012/0053838 | A1 | 3/2012 | Andrews et al. |
| 2012/0090835 | A1 | 4/2012 | Kefi |
| 2013/0154847 | A1 | 6/2013 | Potyrailo et al. |

OTHER PUBLICATIONS

Hess, et al., "Development of a downhole instrument for measuring real-time concentration of ionic species in geothermal wells," for American Chemical Society Spring 2014 Meeting, Report No. SAND2014-2114C 505345, published on Mar. 1, 2014, 22 pg.*

U.S. Appl. No. 14/660,702, filed Mar. 17, 2015, Hernandez-Sanchez et al.
U.S. Appl. No. 14/509,929, filed Oct. 8, 2014, Anderson et al.
U.S. Appl. No. 14/502,821, filed Sep. 30, 2014, Cieslewski et al.
U.S. Appl. No. 14/488,989, filed Sep. 17, 2014, Cannan et al.
U.S. Appl. No. 15/336,296, filed Oct. 27, 2016, Boyle et al.
U.S. Appl. No. 14/168,543, filed Jan. 30, 2014, Boyle.
U.S. Appl. No. 14/069,487, filed Nov. 1, 2013, Dirk et al.
U.S. Appl. No. 15/010,899, filed Jan. 29, 2016, Boyle.
Abdel-Latif MS et al., "A novel potentiometric solid-state iodide sensor," *Anal. Lett.* Mar. 2007:40(4):729-36.
Axelsson G et al., "Analysis of tracer test data, and injection-induced cooling, in the Laugaland geothermal field, N-Iceland," *Geothermics* Dec. 2001;30(6):697-725.
Arida Ham et al., "A new cesium ion selective graphite rod electrode based on Cs-molybdophosphate," *Anal. Lett.* 2004;37(1):21-33.
Bilal BA et al., Potentiometric determination of the activity of fluoride ion in aqueous solutions at high pressure and high temperature, *Fresenius Z Anal. Chem.* 1988;330:8-10.
Buck RP, "Ion selective electrodes," *Anal. Chem.* Apr. 1978;50(5):17R-29R.
Coetzee CJ et al., "A potentiometric determination of cesium ion," *Anal. Chim Acta* Sep. 1971;56(2):321-4.
Kumagai N. et al., "Characterization of geothermal fluid flows at Sumikawa geothermal area, Japan, using two types of tracers and an improved multi-path model," *Geothermics* Jun. 2004;33(3):257-75.
Niedrach LW, "A new membrane-type pH sensor for use in high temperature-high pressure water," *J. Electrochem. Soc.* Oct. 1980; 127(10):2122-30.
Rajbhandari N. et al., "Characterization of home-made silver sulphide based iodide selective electrode," *Talanta* Sep. 15, 2010;82(4):1448-54.

* cited by examiner

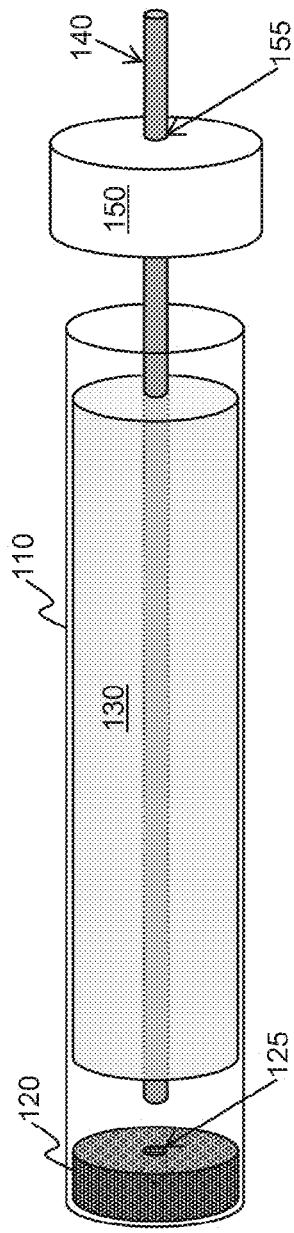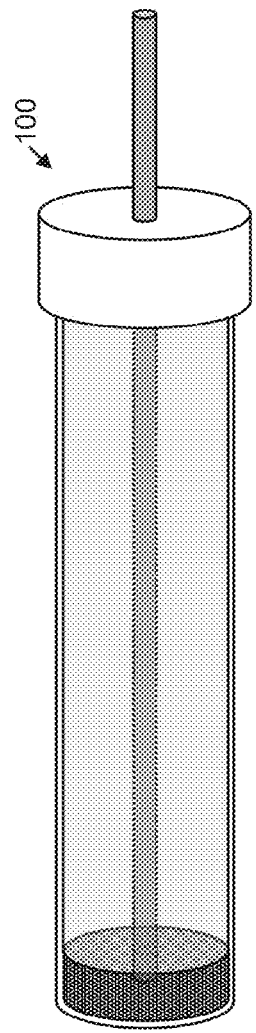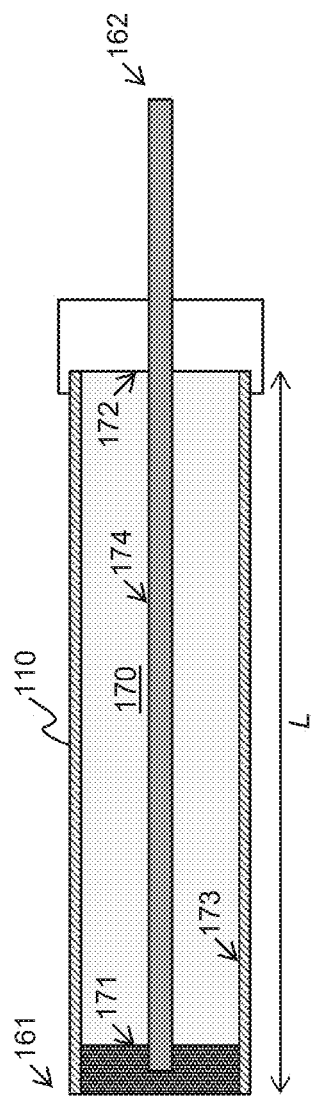

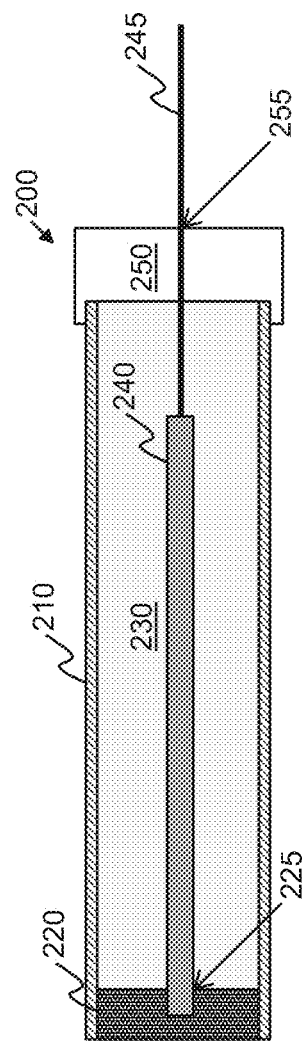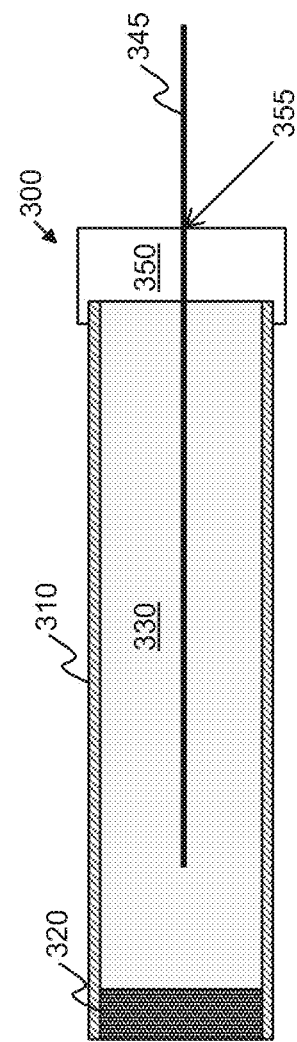
FIG. 3A
FIG. 3B

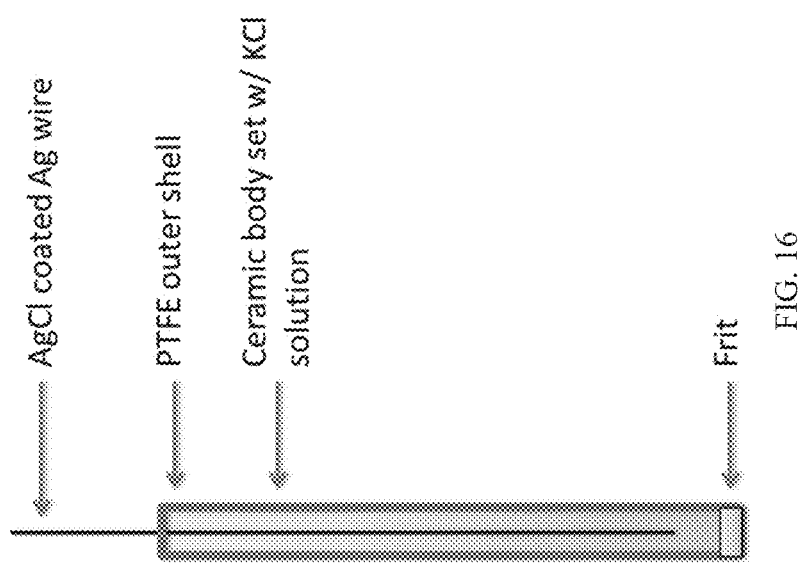

RUGGEDIZED DOWNHOLE TOOL FOR REAL-TIME MEASUREMENTS AND USES THEREOF

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to ruggedized downhole tools and sensors, as well as uses thereof. In particular, these tools can operate under extreme conditions and, therefore, allow for real-time measurements in geothermal reservoirs or other potentially harsh environments.

BACKGROUND OF THE INVENTION

Geothermal energy provides an alternative sustainable energy source. Harnessing such energy requires an understanding of geothermal reservoir properties, such as the extent and interconnectivity of subsurface rock networks, characteristics of various geologic formations, and chemical analyses of existing and injected fluids within geothermal wells.

Enhanced or Engineered Geothermal Systems (EGS) extract heat by circulating fluid through subsurface fracture networks in a geothermal reservoir. An EGS plant generally includes an injection well that injects fluid into high temperature fractures within the reservoir and numerous production wells that pump the hot geothermal brine to the surface. The thermal energy from the geothermal brine is then converted into electricity, and the spent brine is then re-injected into the reservoir via injection wells.

In order to develop and maintain EGS plants, tracer experiments are generally used to characterize the fracture networks. Most tracer experiments involve injecting a tracer at the injection well, manually collecting liquid samples at the wellhead of the production well, and sending the samples off-site for laboratory analysis. While this method provides accurate tracer concentration data at very low levels of detection, it does not provide information regarding the location of the fractures that were conducting the tracer between wellbores.

Real-time measurements could provide location-specific information for tracer experiments. However, due to the harsh conditions present in these wellbores, any useful sensor or tool should be able to withstand excessive temperature, pressure, and/or pH. New sensors and tools capable of operating under harsh conditions for geothermal reservoirs and providing real-time measurements are needed.

SUMMARY OF THE INVENTION

Accordingly, the present invention includes electrode tools and apparatuses that allow for downhole measurements in geothermal environments. This technology is based on ion selective electrodes and pH probes that are stable under high temperature and high pressure conditions. The ion selective electrode can be adapted with ion selective materials that permit selective conduction of the ion of interest. For instance, if the ion of interest is fluoride, then the ion selective material can be any membrane that permits conduction of fluoride through its pores or crystal lattice. In particular embodiments, the sensors are ruggedized by employing a solid state electrode, rather than a liquid-based electrode system. Of course, while designed for rugged downhole use, the tools of the present invention can also be used to take measurements at the wellhead, as well as applied to harsh environments present in oil and gas wells.

For understanding hydro-fracture networks, the present invention allows for the acquisition of tracer data that tells the operator at what depth and time the tracer appeared in the wellbore. As shown in FIG. 1, tracer studies are generally conducted by injecting a tracer 41 with injected water 40 into an injection well 10. The injected water travels through hydro-fractures 30 in the reservoir, thereby collecting heat, and then flows to a production well 20. Tracer concentration can be measured in two ways. First, the tracer concentration can be determined at the wellhead 51, thereby providing an integrated tracer concentration. Alternatively, the tracer concentration can be determined as a function of depth, e.g., as a function of the location of each fracture zone 52. This depth-specific information is an advance on current technology, where all tracer concentration data is measured at the wellhead, such that the operator has no knowledge of what depth the tracer entered the wellbore.

The present invention also allows for the measurement of pH at depth in the wellbore. Current technology requires that the pH sample be taken at the surface or that a sample tool be inserted into the wellbore in order to bring a sample to the surface. Both of these methods involve difficult sample processing to reconstruct what the sample would have been like at depth. Accordingly, the present invention also encompasses ruggedized pH electrodes (e.g., any described herein) for real-time measurements.

Accordingly, in one aspect, the invention features an ion selective electrode (e.g., a ruggedized ISE for high temperature and/or high pressure conditions) having an electrode body including a temperature-resistant material, where the electrode body includes an inner volume, a proximal end, and a distal end; a pressure fitting cap disposed at the distal end of the electrode body; an ion selective material (ISM) disposed at the proximal end of the electrode body; an electron conductor disposed within the electrode body and electrically connected to the ISM, where the electron conductor includes a conductive material that extends along at least a portion of an axial length of the electrode body (e.g., or extends along the entire axial length); and a potting material including a solid, non-conductive material disposed within the electrode body, where the potting material conforms to fill the inner volume (e.g., the entire inner volume) confined by a surface of the ISM and a surface of the pressure fitting cap.

In another aspect, the invention features a reference electrode (e.g., a ruggedized reference electrode for high temperature and/or high pressure conditions) having an electrode body including a temperature-resistant material, where the electrode body includes an inner volume, a proximal end, and a distal end; a pressure fitting cap disposed at the distal end of the electrode body; a frit disposed at the proximal end of the electrode body; an electron conductor disposed within the electrode body, where the electron conductor includes a conductive material that extends along at least a portion of an axial length of the electrode body (e.g., or extends along the entire axial length); and a potting material including a solid material (e.g., a ceramic set in an electrolyte solution) disposed within the electrode body, where the potting material conforms to fill the inner volume (e.g., the entire inner volume) confined by a surface of the frit and a surface of the pressure fitting cap.

In yet another aspect, the invention features an integrated apparatus for measurements in high temperature and/or high pressure conditions, the apparatus including a ruggedized ion selective electrode (e.g., any described herein), a ruggedized reference electrode (e.g., any described herein), a ruggedized pH electrode (e.g., any described herein), and an electronic module.

In some embodiments, the ruggedized reference electrode includes an electrode body, an electron conductor disposed within the electrode body, a frit disposed at a proximal end of the electrode body, and a potting material disposed within the electrode body (e.g., where the potting material conforms to fill an inner volume (e.g., the entire inner volume) of the electrode body and includes an electrolyte, such as any described herein).

In other embodiments, the ruggedized pH electrode includes a ceramic electrode body, an electron conductor disposed within the electrode body, and a metal material disposed within the electrode body (e.g., where the metal material conforms to fill an inner volume of the electrode body, such as the entire inner volume).

In some embodiments, the electronic module is configured to receive one or more potential measurements from the ion selective electrode, reference electrode, and/or pH electrode. In yet other embodiments, the electronic module includes any other useful component (e.g., an analog multiplexer configured to receive the one or more potential measurements and to output an analog measurement signal, an analog-to-digital converter (ADC) configured to receive an analog measurement signal and to output a digital measurement signal, and/or a microprocessor configured to control the sensor(s), an analog multiplexer, and/or an ADC and to output an encoded signal to a logging wireline).

In some embodiments, the integrated apparatus has five primary sensors: an ion selective electrode, a pH probe, a reference electrode, a temperature probe (e.g., a thermocouple), and a pressure probe. Optionally, the apparatus can include a flow rate sensor. In one embodiment, all sensors are configured to withstand the high temperature, high pressure, and corrosive environment found in geothermal wells.

In another aspect, the invention features a method for real-time monitoring of conditions in a geothermal reservoir. The method includes deploying a ruggedized ion selective electrode or an integrated apparatus (e.g., any described herein) into the geothermal reservoir having one or more hydro-fracture zones, where the ion selective electrode or apparatus is configured to measure a concentration of an ion tracer; and measuring one or more concentrations in real-time as a function of depth of the geothermal reservoir.

In some embodiments, the method further includes correlating the concentrations with a location of the one or more hydro-fracture zones. In other embodiments, the method includes, prior to the deploying step, injecting an ion tracer into an injection well or a wellbore of the geothermal reservoir, where the deploying step includes deploying the ion selective electrode or the apparatus into a production well of the geothermal reservoir.

In yet another aspect, the invention features a method of fabricating a ruggedized electrode for high temperature and/or high pressure conditions, the method including: (i) providing an electrode body having an inner volume, a proximal end, and a distal end; (ii) disposing an ion selective material or a frit at the proximal end of the electrode body; (iii) disposing an electron conductor within the inner volume, where steps (ii) and (iii) can be performed in any order or at the same time; (iv) injecting a potting material (e.g., a non-conductive epoxy) in liquid form into the inner volume; (v) placing a pressure fitting at the distal end of the electrode body, where step (v) can be performed prior to step (iv); and (vi) curing the potting material, thereby proving a solid potting material within the electrode body.

For any embodiment herein, the electrode body includes a tube having an axial length.

For any embodiment herein, the potting material can include one or more materials (e.g., any described herein, such as an epoxy, such as a conductive epoxy or a non-conductive epoxy; an adhesive, such as a high temperature adhesive; a cermet; or a ceramic, as well as alloys or stabilized forms thereof).

For any embodiment herein, the ISM can include a ceramic, a membrane, a crystal, or a pellet in any useful form (e.g., a disk, a membrane, etc.). In some embodiments, the ISM includes an iodide-selective material (e.g., includes Ag). In further embodiments, the ISM includes a recessed portion configured to receive a proximal end of the electron conductor and optionally includes a conductive adhesive disposed within the recessed portion and between the ion selective material and the electron conductor.

For any embodiment herein, the electrode body includes a temperature-resistant polymer, ceramic, metal, or a combination thereof (e.g., any described herein, such as stainless steel or a polyether).

For any embodiment herein, the electrode further includes a lead wire electrically connected to the electron conductor and optionally includes the lead wire to be electrically connected to a meter, electronics, a wireline, or other circuitry.

For any embodiment herein, the ion selective electrode or apparatus includes an electronic module (e.g., including a high temperature level shifter configured to receive one or more signals from the ion selective electrode, reference electrode, and/or pH electrode and to transmit one or more shifted signals; an analog multiplexer configured to receive the one or more shifted signals from the level shifter and to transmit one or more multiplexed analog signals; an analog-to-digital converter configured to receive the one or more multiplexed analog signals and to transmit one or more digital signals; a microprocessor configured to receive the one or more digital signals and to transmit the one or more digital signals to a receiver; and/or a receiver is located uphole of the ion selective electrode).

For any embodiment herein, the ion selective electrode or apparatus includes a high temperature level shifter circuit (e.g., configured to receive one or more electronic signals from the ion selective electrode, reference electrode, and/or pH electrode and to provide one or more shifted electronic signals). In particular embodiments, the high temperature level shifter circuit includes a driver circuit configured to generate a square wave signal; an inverter circuit configured to receive the square wave signal and generate a negative voltage signal; an operational amplifier buffer circuit configured to receive the negative voltage signal and comprising an input configured to receive the one or more potential measurements from the ion selective electrode, reference electrode, and/or pH electrode, thereby providing one or more buffered output signals; and a summing circuit configured to receive the one or more buffered output signals and to generate one or more shifted signals.

Definitions

As used herein, the term "about" means +/−10% of any recited value. As used herein, this term modifies any recited value, range of values, or endpoints of one or more ranges.

As used herein, the terms "proximal," "distal," "top," "bottom," "upper," "lower," "above," and "below" are used to provide a relative relationship between structures. The use of these terms does not indicate or require that a particular structure must be located at a particular location in the electrode or apparatus.

Other features and advantages of the invention will be apparent from the following description and the claims.

BRIEF DESCRIPTION OF THE DRAWINGS

FIG. 2A-2C shows schematics for an exemplary ion selective electrode (ISE) 100 in (A) an exploded view, (B) an assembled view, and (C) a cross-section view.

FIG. 3A-3B shows schematics for (A) another exemplary ISE 200 and (B) an exemplary reference electrode 300.

FIG. 16 is a schematic of an exemplary high temperature reference electrode.

DETAILED DESCRIPTION OF THE INVENTION

Figure 1:
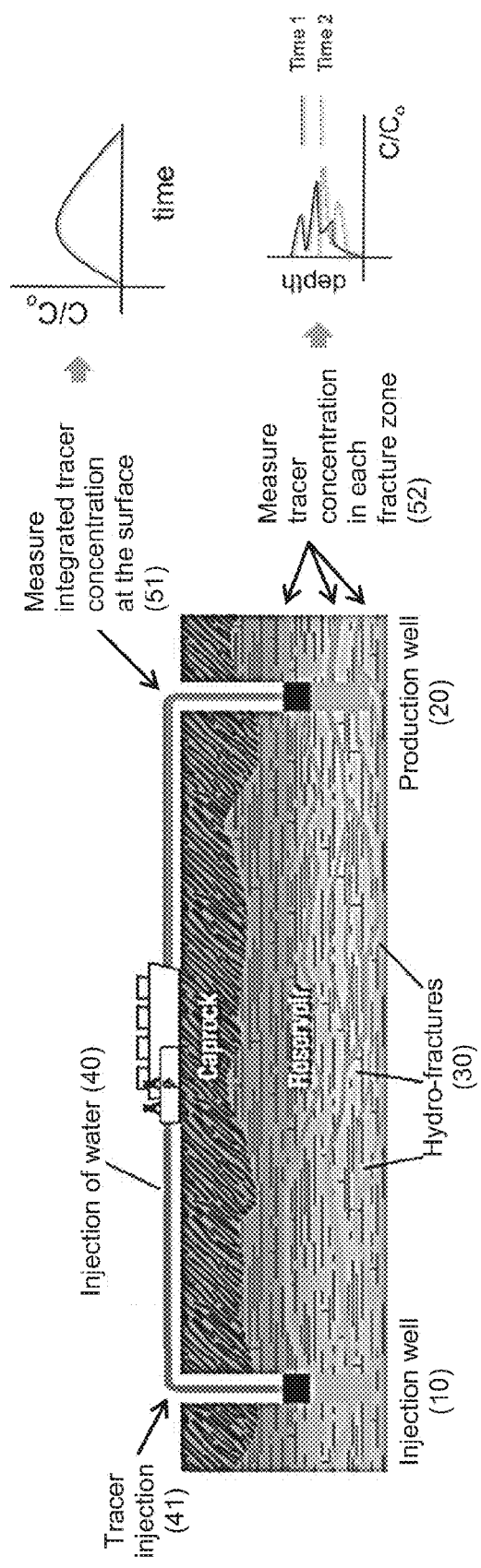
FIG. 1 is a schematic showing an exemplary method for monitoring conditions in a geothermal reservoir.

The present invention is directed to ruggedized sensors (e.g., electrodes) for conducting measurements. In particular embodiments, the sensors allow for real-time measurements within a geothermal well and, therefore, are configured to facilitate measurements of relevant analytes in harsh conditions present in the well. Additional details of ruggedized electrodes, tools, and related materials and methods are described herein.

Ion Selective Electrode

The present invention includes a ruggedized ion selective electrode (ISE) to measure one or more ions (e.g., from an ion tracer, such as any herein). Generally, the ISE includes an ion selective material (ISM) for the ion to be measured, as well as an electron conductor electrically connected to the ISM. To establish an electrical connection between the ISM and electron conductor, a conductive adhesive (e.g., any described herein) can be used to attach these two components. In addition, if the ISM is in pellet form, then a recess can be provided in the pellet to promote an electrical connection with the electron conductor.

The electron conductor can be provided in any useful material and form (e.g., any described herein). For instance, the electron conductor can be made from any useful conductive material. Exemplary conductive materials include graphite or a conductive metal (e.g., tungsten, nickel, and/or platinum) in any useful form, such as a wire and/or rod form. In addition, the electron conductor can be configured to connect electrically the ISM that provides ion selectivity with a meter that detects the potential difference between the ISE and a reference electrode (e.g., any useful reference electrode, such as any described herein). To facilitate these connections, the electron conductor can be connected electrically to a lead wire, which in turns connects to the meter. Any of these connections can include any useful pressure fittings (e.g., any described herein).

The ISM and electron conductor is provided within an electrode body, which is generally composed of a temperature-resistant, rigid material. Exemplary temperature-resistant, rigid materials include steel, such as stainless steel, or any other useful material described herein.

Within the electrode body, the potting material (e.g., any described herein) fills the remaining inner volume. This inner volume is generally bounded and confined by a surface of the ISM at the proximal end of the electrode body and a surface of the pressure fitting cap, which is located at the distal end of the electrode body.

FIG. 2A-2C provides an exemplary ISE 100 having an electrode body 110, an ISM 120 located at the proximal end 161 of the electrode body, and a pressure fitting 150 located at the distal end 162 of the electrode body. As can be seen in FIG. 2C, an electron conductor 140 extends along at least a portion of an axial length L of the electrode body. In some non-limiting embodiments, the electron conductor 140 can extend along the entire axial length L and then emerge through an orifice 155 in the pressure fitting 150. Alternatively, as shown in FIG. 3A, the electron conductor 240 can extend along a portion of axial length L and then be electrically connected to a lead wire 245 that extends into the electrode body 210. Thus, any useful configuration can be employed so long as electrical connection is maintained between the ISM, the electron conductor, and the meter.

To facilitate connection between the ISM 120 and the electron conductor 140, a recessed portion 125 can be present, which can optionally include a conductive adhesive to connect electrically the ISM to the electron conductor.

In certain embodiments, the electrode body is characterized by an inner volume. This inner volume can include any volume remaining within the electrode body after placement of the ISM, the electron conductor, and/or the pressure fitting. In certain embodiments, the electrode body 110 includes a tube having an inner volume 170 disposed within the tube. In particular embodiments, the inner volume 170 is confined by a distal surface 171 of the ISM 120, the inner surface 173 of the electrode body 110, and the proximal surface 172 of the pressure fitting cap. In addition, the inner volume 170 excludes the volume enclosed by the surface 174 of the electron conductor 140. In some embodiments, the potting material 130 fills the entire inner volume. In other embodiments, the potting material fills a significant portion of the inner volume (e.g., from about 50% to about 100% of the inner volume). In yet other embodiments, two or more potting materials are employed within the inner volume. In some embodiments, the potting material(s) form a solid within the ruggedized electrode.

The ISE can have any useful configuration. FIG. 3A provides an exemplary ISE 200 having an electrode body 210, an ISM 220 disposed at the proximal end, an electron conductor 240 disposed within a recessed portion 225, a lead wire 245 electrically connected to the electron conductor and emerging from an orifice 255 in a pressure fitting 250, and a potting material 230.

In particular embodiments, the electrode of the invention (e.g., an ISE, a reference electrode, or pH electrode) is configured to be ruggedized by employing a potting material that is solid and capable of withstanding high temperatures and/or pressures (e.g., any potting material described herein). Further considerations to provide a ruggedized electrode include use of other temperature- and pressure-resistant materials, such as an electrode body formed from a temperature-resistant and/or fracture-resistant material (e.g., any temperature-resistant, rigid material described herein, such as stainless steel or a polyether), an ISM formed from materials having melting temperatures above conditions in wellbores (e.g., solid state crystals), an electron conductor in rod form, a pressure fitting configured to withstand high pressure and/or temperature, and/or high temperature electronics (e.g., any described herein). Furthermore, changes in ion selective material composition, dimensions, and/or density can be employed to lower the limit of detection at high temperature or pressure conditions. Additionally, the use of high temperature stable conducting polymers between the ion selective membrane and metal rod (e.g., thereby acting as a transducer) can be employed to further lower the limit of detection and enhance performance.

Reference Electrode

The present invention also includes a ruggedized reference electrode for use with a sensing electrode (e.g., an ISE or pH electrode, such as any herein) in order to determine a potential difference. In particular embodiments, the reference electrode includes a solid potting material set with an electrolyte (e.g., a KCl solution) to provide a ruggedized configuration for use in harsh environments.

FIG. 3B provides an exemplary reference electrode 300 having an electrode body 310, a frit 320 located at the proximal end of the electrode body, and a pressure fitting 350 located at the distal end of the electrode body. An electron conductor 345 extends along at least a portion of an axial length L of the electrode body and then emerges through an orifice 355 in the pressure fitting 350. A potting material 330 includes an electrolyte, and this combination is then disposed within the inner volume of the electrode body 310. FIG. 16 provides an exemplary reference electrode including an Ag/AgCl electron conductor and a potting material of a ceramic set with an electrolyte, i.e., a KCl solution.

The electrode body can be formed from any temperature-resistant, rigid material (e.g., such as any described herein, including stainless steel). In other embodiments, the electrode body for the reference electrode can include zirconium or a zirconium alloy (e.g., Zircaloy-2 alloy having ≥95 wt. % Zr, 1.2-1.7 wt. % Sn, 0.07-0.2 wt. % Fe, 0.05-0.15 wt. % Cr, and 0.03-0.08 wt. % Ni; or Zircaloy-4 having ≥95 wt. % Zr, 1.2-1.7 wt. % Sn, 0.12-0.18 wt. % Fe, 0.05-0.15 wt. % Cr, and ≤0.007 wt. % Ni).

The frit can be composed of any useful material that allows ion conduction but does not permit bulk mixing. Useful materials include a ceramic, a membrane, a pore, or an ISM (e.g., any described herein). Exemplary materials include zirconia and stabilized or partially stabilized zirconia, such as yttria- calcia-, magnesia-, ceria-, alumina-, or hafnia-stabilized zirconias.

The potting material can include any material that stabilizes the electrolyte, such as a ceramic, including zirconia ($ZrO_2$), alumina ($Al_2O_3$), silica ($SiO_2$), as well as alloys or stabilized forms thereof. In particular, the potting material (e.g., as a powder, granule, or fiber) can be blended, saturated, or set with an electrolyte in solid (e.g., crystal or granular forms) or in liquid (e.g., aqueous solution) forms. Exemplary electrolytes include alkali halides, such as KCl or NaCl in crystal or solution form.

The electron conductor can be formed from any useful temperature-resistant material (e.g., Ag, Pt, Zr, composite ceramic-metal material (i.e., a cermet), or stabilized zirconia) optionally coated in a metal salt (e.g., AgCl or $ZrO_2$), such as Ag/AgCl or $Zr/ZrO_2$ (e.g., any described herein).

pH Electrode

The present invention also includes a ruggedized pH electrode having solid state components. An exemplary ruggedized pH electrode includes a ceramic electrode body (e.g., any ceramic described herein), an electron conductor disposed within the electrode body (e.g., any conductor described herein, such as Ag, Pt, Zr, etc., including Ag/AgCl or $Zr/ZrO_2$), and a metal material disposed within the electrode body, where the metal material conforms to fill an inner volume of the electrode body. In some embodiments, the metal material fills the entire inner volume, thereby providing an electrical connection between the ceramic electrode body and the electron conductor.

The ceramic electrode body can be formed of a temperature-resistant material that allows for conduction of an ion that correlates with pH of the test solution. For instance, such a material includes yttria-stabilized zirconias, which conduct oxygen ions that, in turn, equilibrate with hydrogen ions in the test solution. In this manner, the measured relative potential of oxygen ion movement within the ceramic (as compared to a relevant reference electrode, such as any herein) can be correlated with the concentration of hydrogen ions or pH. Exemplary materials for the ceramic electrode body include stabilized zirconia (e.g., $ZrO_2$ stabilized with yttria $Y_2O_3$, scandia $Sc_2O_3$, calcia CaO, gadolinia $Gd_2O_3$, strontia SrO, or magnesia MgO), doped thoria (e.g., $ThO_2$ doped with $Y_2O_3$, $La_2O_3$, or $Sm_2O_3$), doped ceria (e.g., $CeO_2$ doped with $Gd_2O_3$, CaO, or $Sm_2O_3$), or doped lanthanum oxide (e.g., $La_2O_3$ doped with MgO or any other dopant herein). Additional ceramics are described in U.S. Pat. No. 4,264,424, which is incorporated herein by reference in its entirety.

The metal material can be any useful reduction-oxidation pair, such as a metal-metal oxide pair (e.g., a Cu/CuO pair, a Ni/NiO pair, or an Hg/HgO pair).

Additional design considerations for pH electrodes are described in Niedrach L W, "A new membrane-type pH sensor for use in high temperature-high pressure water," *J. Electrochem. Soc.* 1980 October; 127(10):2122-30; U.S. Pat. Nos. 4,264,424, 4,406,766, and 4,575,410; and U.S. Pub. No. 2009-0050476, each of which is incorporated herein by reference in its entirety.

Potting Material

The potting material for the electrode can be any useful material, including mixtures of materials. In particular, such potting materials are capable of withstanding harsh conditions, such as extreme temperature, pressure, and/or pH. In some embodiments, the potting material forms a solid mass within the electrode body (e.g., such as by using a curable resin, such as curable epoxy). In other embodiments, the potting material is non-conductive, such as in the ion selective electrode. In yet other embodiments, the potting material is admixed with an electrolyte, such as in a reference electrode.

Exemplary potting materials include an epoxy, such as a conductive epoxy or a non-conductive epoxy; an adhesive, such as a high temperature adhesive; a cermet; or a ceramic, such as zirconia ($ZrO_2$), alumina ($Al_2O_3$), silica ($SiO_2$), as well as alloys or stabilized forms thereof.

Exemplary epoxies include an epoxy resin (e.g., a bisphenol A epoxy resin) optionally including a co-reactant (e.g., an acid anhydride or an amine complex), such as commercially available high-temperature, non-conductive epoxies (e.g., Duralco™ 4460 with 600° F. maximum use temperature and having a Shore D hardness of 90, viscosity of 600 cps, tensile strength of 10,300 psi, and dielectric strength of 500 volts/mil and can employ an acid anhydride hardener; Duralco™ 4703 with 650° F. maximum use temperature and having a Shore D hardness of 95, viscosity of 50,000 cps, tensile strength of 11,800 psi, and dielectric strength of 450 volts/mil, where this resin is a composite of epoxy and ceramic particles (e.g., $Al_2O_3$ having a 44 μm particle size) and can employ an amine complex hardener; and Duralco™ 4700 with 600° F. maximum use temperature and having a Shore D hardness of 94, viscosity of 40,000 cps, tensile strength of 11,100 psi, and dielectric strength of 550 volts/mil, where this resin is a composite of epoxy, metal, and ceramic particles (e.g., $Al_2O_3$ having a 44 μm particle size) and can employ an amine complex hardener, and where each is available from available from Cotronics Corp., Brooklyn, N.Y.); and high-temperature, conductive epoxies including conductive particles, such as silver, nickel, aluminum, ceramic, or graphite (e.g., Duralco™ 120 with 500° F. maximum use temperature and having a Shore D hardness of 70, viscosity of 25,000 cps, volume resistance of 0.00008 ohm·cm, compressive strength of 6,000 psi, and flexural strength of 1,150 psi, where this resin is a composite of epoxy and ultrafine silver and uses a hardener; Duralco™ 124 with 650° F. maximum use temperature and having viscosity of 20,000 cps, volume resistance of 0.002 ohm·cm, and thermal conductivity of 50 BTU·in/hr·° F.·ft², where this resin is a composite of epoxy and ultrafine silver and uses a hardener; and Duralco™ 125 with 450° F. maximum use temperature and having viscosity of 50,000 cps, volume resistance of 0.002 ohm·cm, and thermal conductivity of 40 BTU·in/hr·° F.·ft², where this resin is a composite of epoxy and ultrafine silver and uses a hardener, where each are available from available from Cotronics Corp., as well as GPC 251 A/B having a volume resistance of 0.0002 ohm·cm at 120° C., tensile strength of 11,200 psi, and thermal conductivity of 6.74 W/mK, where this resin is a composite of bisphenol A epoxy resin and silver (70-75 wt. % silver of maximum particle size of 33 μm and typical particle size of 15 μm) and uses a curing agent or hardener, available from Creative Materials, Inc., Ayer, Mass.).

Potting materials can include ceramics, such as high-temperature, non-conductive ceramics, e.g., having an alumina, zirconia, magnesia, zircon, or mica base. Exemplary ceramics include Resbond™ 919 with 2800° F. maximum use temperature and having a compressive strength of 4,500 psi, flexural strength of 450 psi, and dielectric strength of 270 volts/mil, where this zirconia adhesive includes a MgO—$ZrO_2$ base and a refractory ceramic colloid binder including silicate, phosphate, alumina, zirconia, and a colloid; and Resbond™ 920 with 3000° F. maximum use temperature and having a compressive strength of 4,500 psi, flexural strength of 450 psi, and dielectric strength of 270 volts/mil, where this alumina adhesive includes an $Al_2O_3$ base and a refractory ceramic colloid binder, as described above, available from Cotronics Corp.

Exemplary cermets include high-temperature, non-conductive cermets having ceramic and metallic materials (e.g., Durapot™ 809 with 2800° F. maximum use temperature and having a thermal conductivity of 4 BTU·in/hr·° F.·ft², volume resistivity of $10^{11}$ ohm·cm, and dielectric strength of 270 volts/mil, where this cermet includes a MgO base and a refractory ceramic colloid binder, as described above; and Durapot™ 810 with 3000° F. maximum use temperature and having a thermal conductivity of 15 BTU·in/hr·° F.·ft², volume resistivity of $10^{11}$ ohm·cm, and dielectric strength of 270 volts/mil, where this cermet includes an alumina base and a refractory ceramic colloid binder, as described above, available from Cotronics Corp.).

Any of these potting materials (e.g., epoxies, ceramics, cermets, adhesives, etc.) can be configured to be electrically conductive by including one or more particles of a conductive material, such as silver, nickel, graphite, steel, etc.

Electron Conductor

The sensors of the invention can include any useful electron conductor. Such electron conductors can be formed of any conductive material(s) that withstand high temperature and/or pressure conditions.

For instance, the electron conductor can be made from any useful conductive material that is optionally temperature-resistant. Exemplary materials include graphite, a conductive metal (e.g., W, Ag, Ni, Pt, Au, Cu, or Zr, including combinations, such as beryllium copper), Hg, a composite ceramic-metal material (i.e., a cermet, such as any described herein), or a ceramic (e.g., stabilized zirconia, or any ceramics described herein) in any useful form, such as a wire and/or rod form. The material can be optionally coated in a salt (e.g., AgCl or $ZrO_2$), such as for Ag/AgCl, $Ag_2S$/Ag, Hg/HgO, or $Zr/ZrO_2$ electron conductors. Methods of making and testing electron conductors are provided in U.S. Pub. No. 2009-0050476, which is incorporated herein by reference in its entirety.

Electrode Body

The sensors of the invention include an electrode body formed from any useful material (e.g., a temperature-resistant material). As described herein, the electrode body can be formed from stainless steel. Alternatively, the electrode body can be formed from a temperature-resistant polymer, ceramic, metal, or combinations thereof (e.g., any described herein).

Furthermore, the electrode body can have any useful configuration. In one example, the electrode body is a tube. In another example, the electrode body includes a connector system (e.g., a single pin feedthru connector system). Such a connector system can include a male member and a female member, the male and female members being releasably connectable to one another, the male member including a conductive pin having a first end and a second end, a sealing annulus circumferentially surrounding a portion of the pin intermediate the ends of the pin, a first refractory covering adjacent the annulus and circumferentially surrounding a portion of the pin between the first end and the annulus, a second refractory covering adjacent the annulus and circumferentially surrounding a portion of the pin between the annulus and the second end of the pin, and a jacket circumferentially surrounding the annulus and portions of the refractory coverings directly adjacent the annulus, the annulus being bonded to the jacket, to the pin and to the refractory coverings. In use, an electron conductor can be connected electrically to the conductive pin (e.g., on the high pressure side, or the side of the male member that releasably connects to the female member (e.g., a boot)), and then an ISM can be connected electrically to the electron conductor. Next, the remaining of the conductor on the high pressure side can be potted in a potting material (e.g., an epoxy, ceramic, or any potting material described herein).

The electrode body can also be a commercially available connector system, such as series K-25 BMASRP, K-25 BM, K-25 BMA, K-25 PM2P, K-16 2P, and K-25 DL2P feedthru connectors, available from Kemlon Products, Pearland, Tex.; and series 107 and 110 receptacles, feedthroughs, plugs, and cable assemblies, available from Teledyne DGO, Inc., Portsmouth, N.H. Additional connector systems are described in U.S. Pat. Nos. 4,077,261, 3,898,731, and 3,793,608, each of which is incorporated herein by reference in its entirety.

The component(s) of the electrode body can include any useful material. Exemplary materials include a heat-resistant polymer, such as a polyether (e.g., polyether ketone or polyaryletherketone), including glass sealed polyether, polysulfone, polyphenylene sulfide, polyetherimide, polyvinylidene fluoride, high performance polyamides (e.g., polyphthalamide), polytetrafluoroethylene, or some other fluorocarbon resin; ceramic, such as glass-bonded ceramic, aluminum oxide, zirconium oxide, a combination of aluminum and silicon oxides, and a combination of aluminum and magnesium silicates; a metal (e.g., 300 series stainless steel, such as 304 S.S, 316 S.S, or 316L grades, or Inconel™, a nickel-chromium-based superalloy); or combinations thereof. Other exemplary materials include stainless steel (e.g., having ≥12 wt. % Cr, such as Fe29Cr4Mo having 28.9 wt. % Cr/4.0 wt. % Mo/0.1 wt. % Ni; E-Brite® 26-1 having 25.7 wt. % Cr/1.0 wt. % Mo/0.1 wt. % Ni, available from Allegheny Technologies Inc., Allegheny, Pa.; and 6X having 20.0 wt. % Cr/6.3 wt. % Mo/26.0 wt. % Ni, where for all these, balance is iron), alloy steels, or carbon steel (e.g., having <12 wt. % Cr); nickel alloys (e.g., Inconel® 625 having 58 wt. % Ni/20-23 wt. % Cr/8-10 wt. % Mo; Hastelloy® C-276 having 57 wt. % Ni/16 wt. % Cr/16 wt. % Mo; Hastelloy® S having 67 wt. % Ni/14.5-17 wt. % Cr/14-16.5 wt. % Mo; and Hastelloy® G having 43 wt. % Ni/28-31.5 wt. % Cr/4-6 wt. % Mo/13-17 wt. % Fe); or other alloys, such as titanium, copper, aluminum, molybdenum, and/or niobium alloys (e.g., Ti50A having 0.008 wt. % C/0.03 wt. % Fe/0.20 wt. % O; Ti0.2Pd having 0.009 wt. % C/0.13 wt. % Fe/0.20 wt. % Pd/0.14 wt. % O; and TiCode 12 having 0.31 wt. % Fe/0.44 wt. % Mo/0.86 wt. % Ni, where for all these, balance is titanium).

Ion Selective Material and Ion Tracers

The present invention includes tools and sensors to detect any useful ion (e.g., a hydrogen ion or an ion tracer). In some embodiments, the ion is an ion tracer useful for characterizing networks of hydro-fractures in geothermal reservoirs. Exemplary ion tracers include a halide ion (e.g., $F^-$, $Br^-$, and $I^-$ in any useful form, such as a halide salt with an alkali cation, including KF, KBr, NaBr, or KI), an alkali cation (e.g., $Li^+$ or $Cs^+$), a hydrogen ion (e.g., $H^+$), as well as any other useful ion.

To measure the target ion, the tools and sensors can include ISMs selective for that ion. The ISM can have any useful form, such as a pellet, a disc, a crystal, a membrane, or a coating made by any useful process, such as by pressing (e.g., into a pellet form), casting (e.g., into a membrane form), thermal spraying (e.g., into a coating form), and/or dip-coating onto a substrate, such as a rod. In particular embodiments, the ISM is configured to have a solid state that can withstand harsh conditions.

Exemplary ions and related ISMs to detect that ion includes an iodide tracer to be detected by an ISM formed of an AgI/$Ag_2S$ pellet; a cesium tracer to be detected by Cs-12-molybdophosphate, cesium tungstoarsenate, or iron hexacyanoferrate; a lithium tracer to be detected by $LiMn_2O_4$; and a fluoride tracer to be detected by $LaF_3$:$Eu^{3+}$ (e.g., EuF$_3$) or a mixture including two or more different rare earth trifluorides (e.g., mixtures including two or more of LaF$_3$, EuF$_3$, DyF$_3$, PrF$_3$, CeF$_3$, and NdF$_3$) in any useful form, such as a pellet or a single crystal. Additional ions and ISMs are described in e.g., as described in Niedrach L W, "A new membrane-type pH sensor for use in high temperature-high pressure water," *J. Electrochem. Soc.* 1980 October; 127(10):2122-30; Bilal B A et al., Potentiometric determination of the activity of fluoride ion in aqueous solutions at high pressure and high temperature," *Fresenius Z Anal. Chem.* 1988; 330:8-10; Coetzee C J et al., "A potentiometric determination of cesium ion," *Anal. Chim. Acta* 1971 September; 56(2):321-4; Arida H A M et al., "A new cesium ion selective graphite rod electrode based on Cs-molybdophosphate," *Anal. Lett.* 2004; 37(1):21-33; Buck R P, "Ion selective electrodes," *Anal. Chem.* 1978 April; 50(5):17R-29R; and U.S. Pat. Nos. 4,021,325, 4,264,424, 4,406,766, 4,575,410, and 4,931,172, each of which is incorporated herein by reference in its entirety.

High Temperature Electronics

The present invention can include an electronics interface that interacts with the sensor(s), such as by measuring, recording, and/or relaying data (e.g., sensor data, such as measured potential difference). Such electronics can include high temperature electronics that can withstand high temperature and pressure environments. For instance, the electronics can be formed from high temperature materials, such as gallium arsenide (GaAs). The electronics interface can have any useful components, such as electrical connections (e.g., a digital and/or analog bus), converters, multiplexers, data storage modules, microprocessor, microcontrollers, etc., including any described in U.S. Pub. Nos. 2011-0215234 and 2010-0044036, as well as U.S. Pat. No. 8,118, 094, each of which is incorporated herein by reference in its entirety.

Any useful high temperature electronic module can be employed to provide one or more useful signals that include sensing information (e.g., one or more potential measurements) from the electrode(s). In particular embodiments, the electronic module includes a high temperature level shifter circuit configured to provide one or more signals (e.g., electronic signals) from the electrodes and to transform these signals to a shifted signal capable of being digitized, encrypted, and/or transmitted in high temperature environments.

Figure 18A:
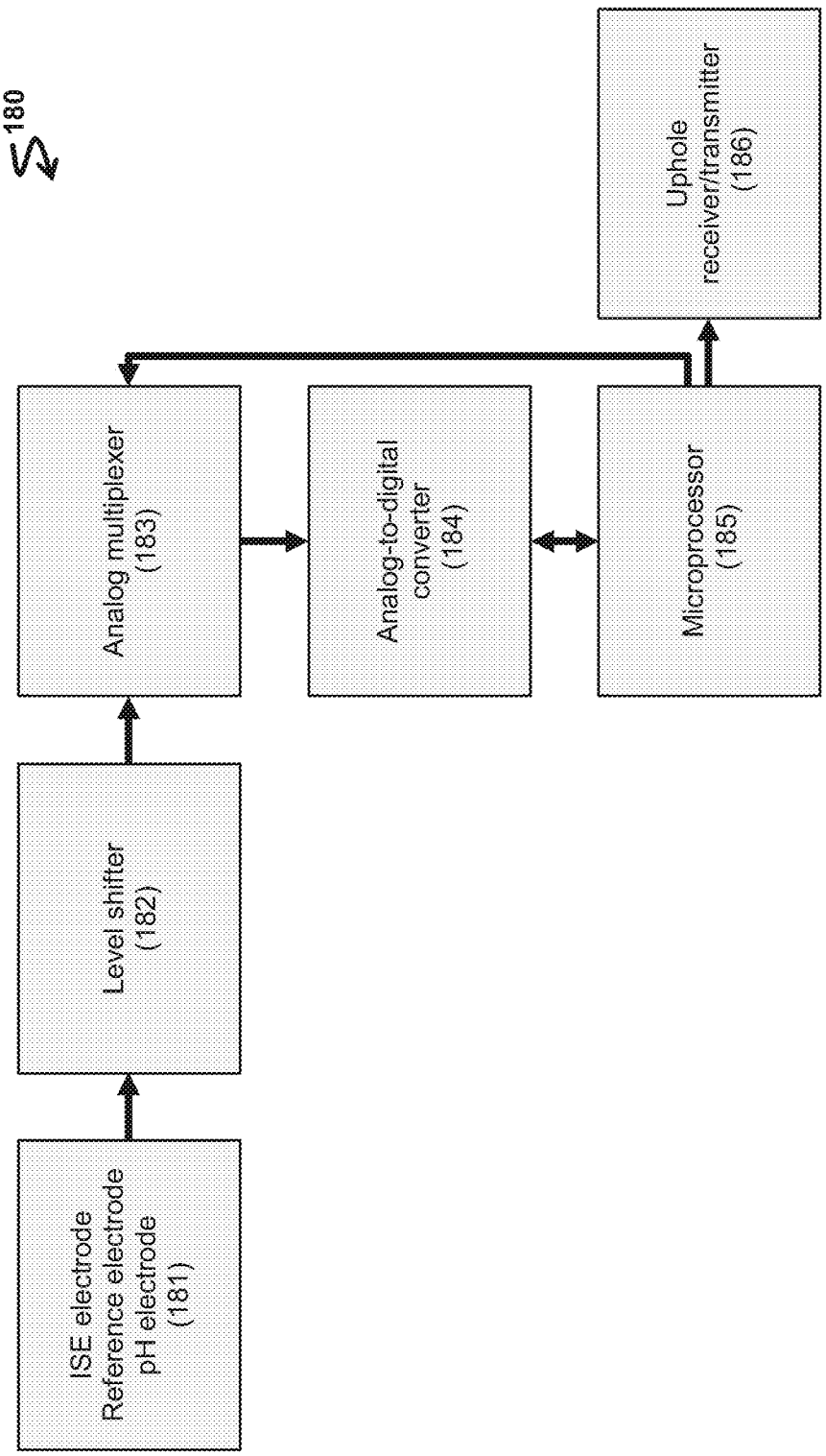
FIG. 18A-18B shows schematics of (A) an exemplary high temperature electronic module 180 and (B) an exemplary level shifter circuit 1820.

FIG. 18A shows a schematic an exemplary high temperature electronic module 180 including a high temperature level shifter 182 configured to receive one or more signals from the ion selective electrode, reference electrode, and/or pH electrode 181; an analog multiplexer 183; an analog-to-digital converter 184; and a microprocessor 185; and an uphole receiver or transmitter 186 (i.e., a receiver or transmitter located outside of the injection well or production well or near the surface opening of such wells). The level shifter 182 configured to receive one or more signals from the ion selective electrode, reference electrode, and/or pH electrode 182 and to transmit one or more shifted signals to the analog multiplexer 183, which in turn is configured to transmit one or more multiplexed analog signals. Then, the analog-to-digital converter 184 converts the one or more multiplexed analog signals into one or more digital signals. In some embodiments, each signal from each electrode is tracked separately, thereby providing a digital signal corresponding to a measurement signal from each electrode. Finally, the microprocessor 185 is configured to receive the one or more digital signals and to transmit the one or more digital signals (e.g., to a receiver). Optionally, the microprocessor 185 is electronically coupled to the analog multiplexer 183.

Figure 18B:
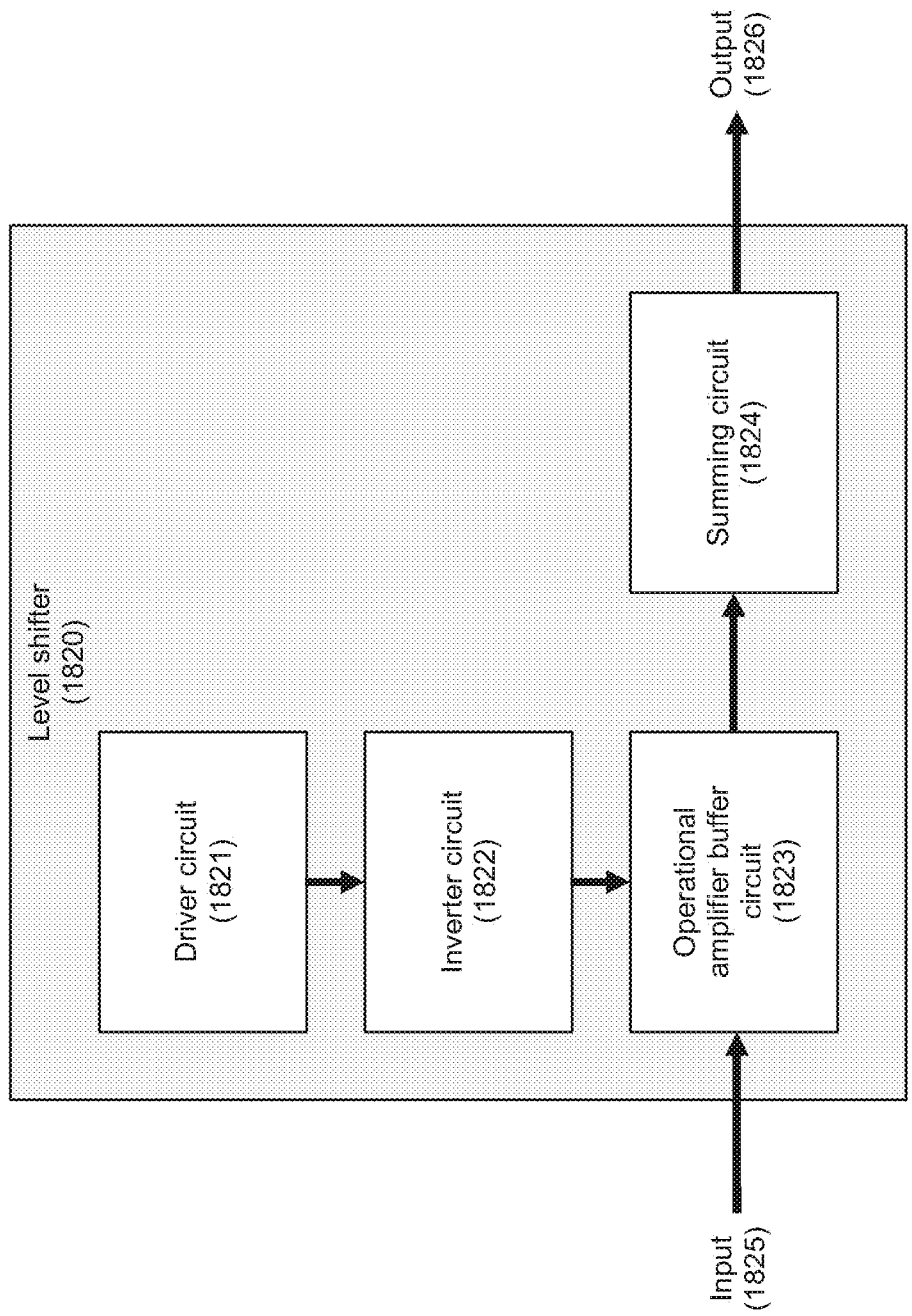

The level shifter circuit can include any useful architecture. In one embodiment, the level shifter circuit 1820 includes a driver circuit 1821, an inverter circuit 1822, an operational amplifier buffer circuit 1823, and a summing circuit 1824, where the input 1825 includes one or more signals from the electrode(s) and the output includes a shifted signal 1826 (FIG. 18B).

In some embodiments, the driver circuit is configured to generate a square wave signal, which in turn is used to generate a negative voltage signal by way of the inverter circuit. Then, the operational amplifier buffer circuit is configured to receive the negative voltage signal, in which the buffer circuit further includes an input configured to receive the one or more potential measurements from the ion selective electrode, reference electrode, and/or pH electrode, thereby providing one or more buffered output signals. Finally, the summing circuit is configured to receive the one or more buffered output signals and to generate one or more shifted signals.

Figure 19A:
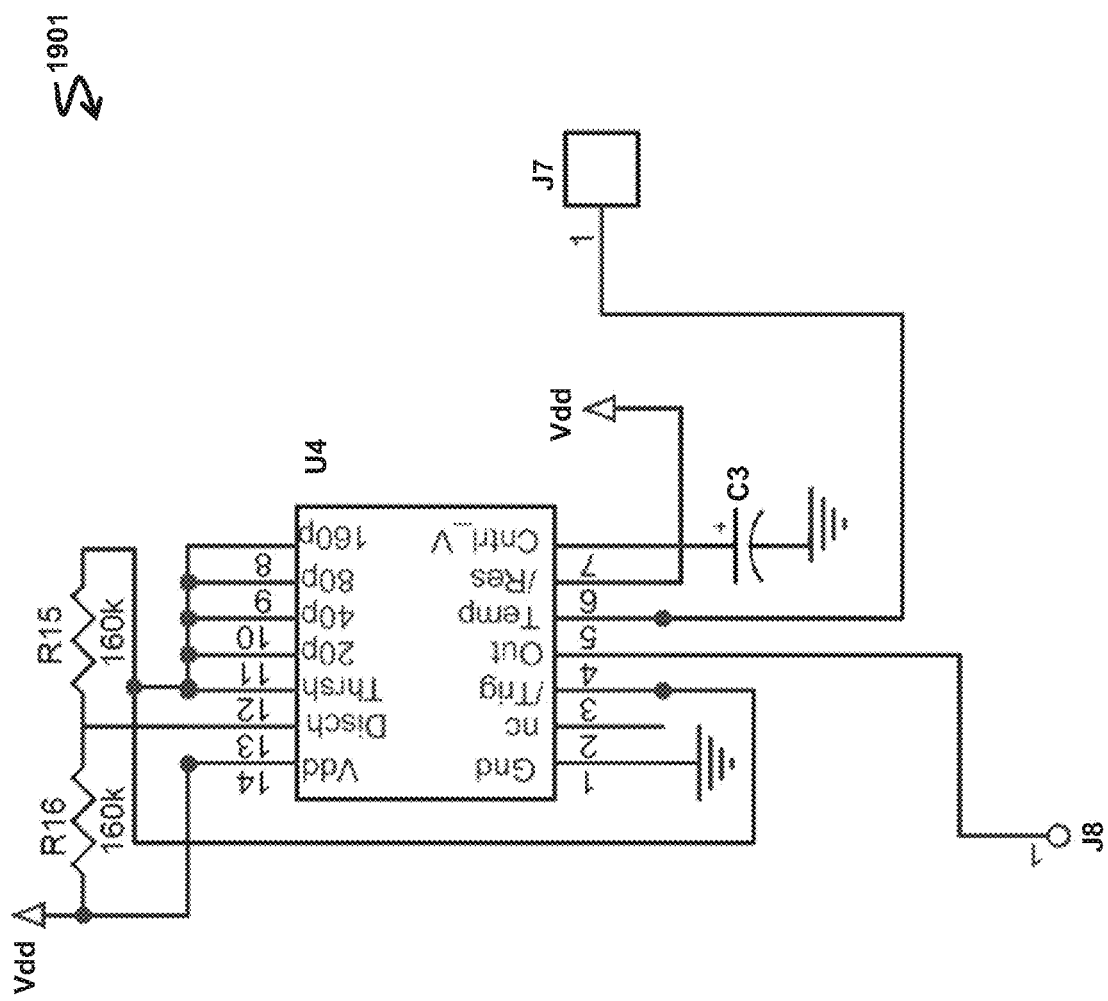
FIG. 19A-19C shows exemplary circuit diagrams of (A) a driver circuit 1901, (B) an inverter circuit 1902, and (C) a combined operational amplifier buffer and summing circuit 1903.
Figure 19B:
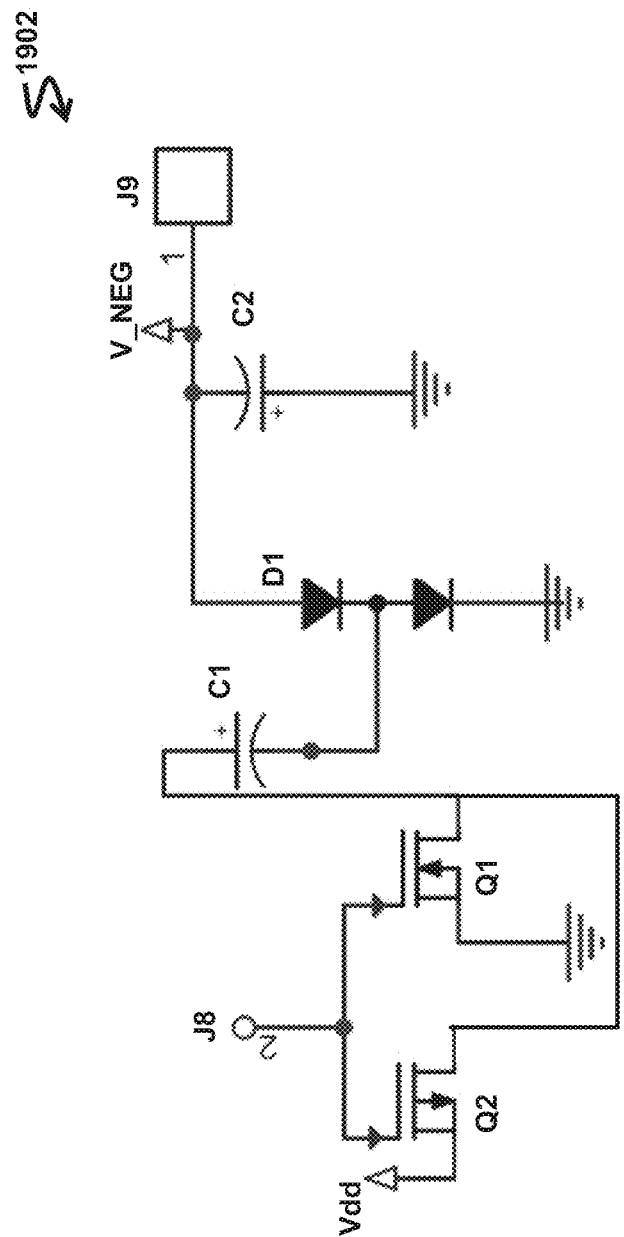
Figure 19C:
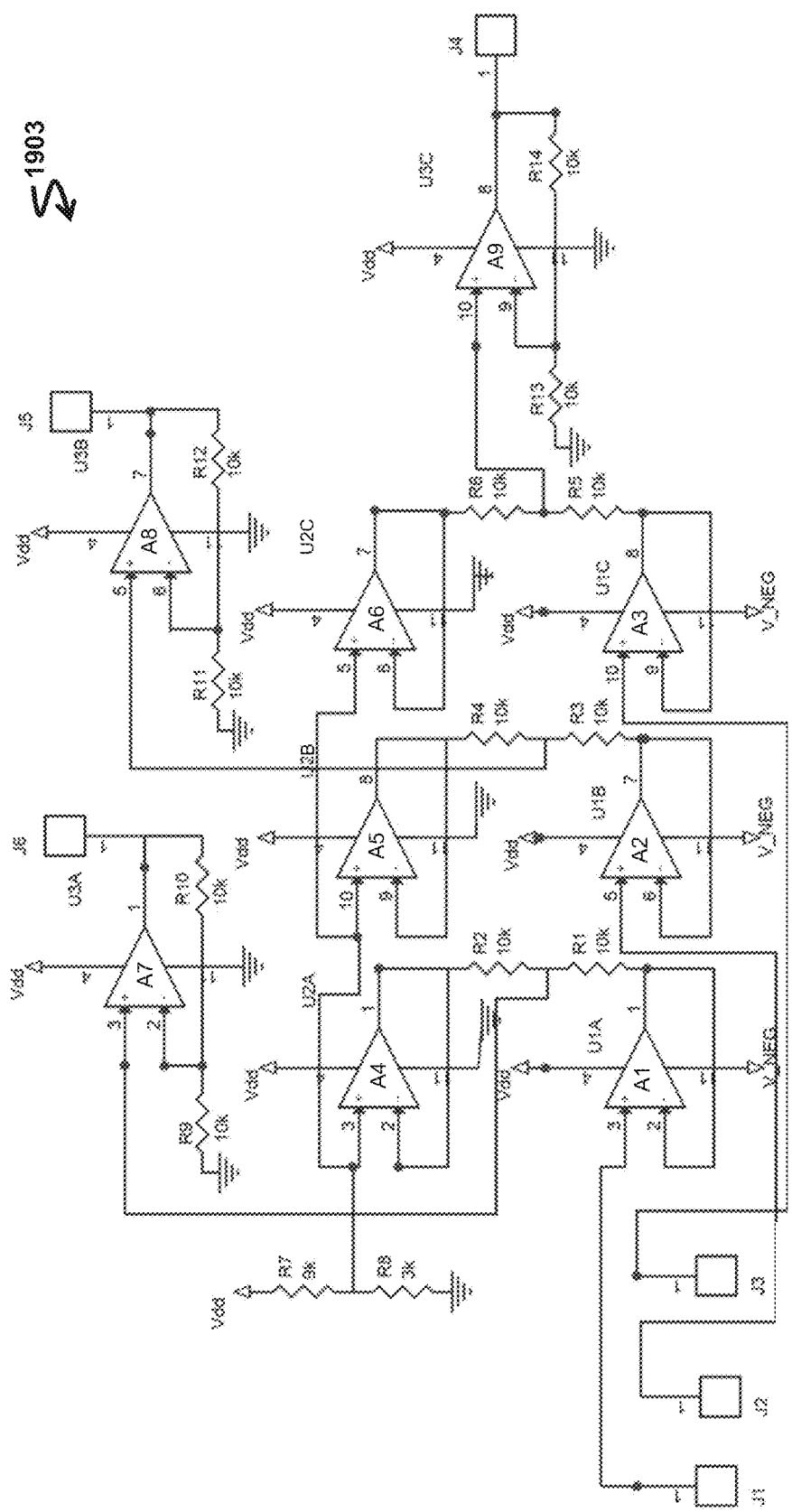

FIG. 19A-19C shows exemplary circuit diagrams of (A) a driver circuit 1901, (B) an inverter circuit 1902, and (C) a combined operational amplifier buffer and summing circuit 1903.

In one embodiment, the level shifter circuit can be used to level shift the measurement signals from the electrodes. In use, the potentials that develop on the electrodes can be level shifted from −1.25 to +1.25V to 0 to +2.5V (e.g., using the circuits in FIG. 19A-19C). To accomplish this, we developed an HT switched capacitor negative voltage generator. The driver circuit 1901 uses a timer U4 (e.g., a CHT-555 timer from Cissoid, Mont-Saint-Guibert, Belgium) in a stable multivibrator configuration to generate a square wave with a desired frequency (FIG. 19A). For these circuit diagrams, J indicates a junction, C indicates a capacitor, R indicates a resistor, Q indicates a transistor, D indicates a diode, and A indicates an amplifier. Then, the square wave is used to drive the inverter circuit 1902 with buffers and to provide power amplification for the square wave (FIG. 19B). Junction J8 from the driver circuit 1901 can be electrically coupled to junction J8 from the inverter circuit 1902. In addition, exemplary transistors Q1 and Q2 can include an n-type and p-type transistor, respectively (e.g., an n-type and p-type MOSFET, such as an NMOS CHT-SNMOS80 transistor and a PMOS CHT-SPMOS30 transistor from Cissoid). The square wave then powers the two capacitor (C1 and C2)/two diode (D1) circuit (e.g., using a CHT-PLA5598C diode from Cissoid) causing the negative voltage to build up on the capacitor C2. Optionally, one or more diagnostic outputs can be generated at junction J9.

Next, the negative voltage (V_NEG) generated by the inverter circuit 1902 along with a positive power rail is used to power the operational amplifier buffer circuit (U1A, U1B, and U1C of circuit 1903 in FIG. 19C). The voltage is then shifted by using the summing circuit (U2A, U2B, U2C, U3A, U3B, and U3C), which adds 1.25V to each signal provided by an electrode at each junction J1, J2, and J3. Thus, signals from junctions J1, J2, and J3 result in shifted signals at junctions J6, J5, and J4, respectively. The shifted voltages are then connected to the analog multiplexer. The microprocessor (e.g., a HT83C51 microprocessor from Honeywell) interfaces with both ADC and analog multiplexer to sequentially digitize the potential from each electrode (e.g., at 30 Hz). After, the data is digitized and then uploaded to the surface.

Integrated Downhole Apparatus

The present invention includes an integrated apparatus having any number of sensors described herein. For instance, the integrated tool can include any electrode described herein, such as an ISE, a reference electrode, and a pH probe. Other components may be present, such as a ruggedized temperature probe (e.g., such as a thermocouple), pressure probe (e.g., such as a pressure transducer), flow rate sensor (e.g., a spinner or propeller electrically connected to a dynamo, such that the dynamo's output correlates with flow velocity), and/or an autonomous surface mounted unit to detect any other useful analytes or tracers (e.g., naphthalene sulfonates, fluorescein tracers, rhodamine tracers, etc.). These components can include high temperature electronics that control these sensors and record the output for these sensors. Furthermore, the integrated apparatus can have one or more electrical connections to facilitate integration with a wireline, thereby allowing recorded data to be transmitted through the wireline and to the operator at the surface of the reservoir and optionally providing power to the integrated downhole apparatus.

Other Components

The sensors and tools herein can include any additional component(s) beneficial for operation. Exemplary components include one or more pressure fittings to encapsulate the elements of the electrode (e.g., one or more pressure fittings at the distal end of any electrode described herein, where the pressure fitting is configured to intimately engage with the electrode body to provide a water-tight cap, such as by employing one or more ferrules, nuts, washers, seals, etc.); heat sinks to conduct heat away from heat-sensitive components and seals, where heat sinks can be formed from any useful material with a high thermal conductivity and a high heat capacity (e.g., copper, silver, platinum, aluminum, gold, etc.); insulators, such as sleeves to protect one or more sensors; tracer injectors, such as those including a reservoir for the tracer, a nozzle to inject a tracer into the wellbore, a pump or valve fluidically connected to the reservoir and the nozzle, and a motor to control the pump or valve, where the tracer injector can be a part of the integrated downhole apparatus (e.g., any useful injector, such as that in U.S. Pat. No. 6,125,934 or U.S. Pub. No. 2010-0044036, each of which is incorporated herein by reference in its entirety); and downhole tool mounting systems, such as that in U.S. Pub. No. 2011-0265584, which is incorporated herein by reference in its entirety.

Methods for Fabricating an Electrode

The present invention encompasses methods of fabricating a ruggedized electrode. The method includes providing an electrode body having an inner volume, a proximal end, and a distal end; disposing an ISM or a frit at the proximal end of the electrode body; disposing an electron conductor within the inner volume; injecting a potting material in liquid form into the inner volume; placing a pressure fitting at the distal end of the electrode body; and curing the potting material.

These steps can be conducted in any order that provides a ruggedized electrode. For instance, to simplify fabrication, the electron conductor and ISM/frit can be first attached together and then disposed within the electrode body. Alternatively, the pressure fitting can first be placed at the distal end of the electrode body, the potting material injected into the electrode body through an orifice of the pressure fitting (and optionally placed under volume to minimize bubble formation), and then the electron conductor can be inserted through the orifice and into the potting material. Any other useful modification can be implemented by a skilled artisan.

Methods for Real-Time Monitoring of Conditions in a Geothermal Reservoir

The electrodes and apparatuses of the invention can be employed for any useful purpose. In one non-limiting example, the method includes real-time monitoring of conditions in a geothermal reservoir. Proper monitoring of geothermal reservoirs is essential for developing and maintaining productivity of the geothermal field. In EGS, tracers are commonly used to characterize the fracture network and determine the connectivity between the injection and production wells. Currently, most tracer experiments require manual sample collection and fail to provide real-time data. In addition, only integrated tracer concentrations are provided because current methodologies also fail to provide tracer concentrations as a function of the location of the fractures. For geothermal reservoirs, any useful sensor must be able to withstand harsh conditions, such as excessive temperature, pressure, and/or pH. Accordingly, the present invention is directed to high-temperature electrochemical sensors capable of measuring tracer concentrations and pH downhole on a wireline tool, as well as methods of deploying such sensors for real-time monitoring of various conditions (e.g., pH and ionic tracer concentration data) at high temperatures (e.g., of from about 100° C. to 350° C., such as more than about 225° C.) and/or at high pressures (e.g., for from about 1000 psi to 5000 psi).

Uses

The present invention encompasses electrodes and apparatuses that are ruggedized to withstand such extreme conditions. Thus, beneficial uses include measurements that must be conducted in extreme conditions, such as in monitoring and maintaining geothermal fields, oil fields, gas fields, etc. Other uses include nuclear well logging, seismic and ultrasonic analyses (e.g., of any field herein), borehole imaging, and monitoring of well conditions (e.g., temperature, pressure, pH, and/or flow patterns using a tracer), as well as any other requiring extreme temperature conditions (e.g., from about 100° C. to about 350° C.), high pressures (e.g., from about 1,000 psi to about 10,000 psi), extended depths (e.g., from about 1,000 feet to about 10,000 feet), and extreme pH (e.g., from about 2 to 11). This technology will also work at the wellhead and in oil and natural gas wells.

EXAMPLES

Example 1: Development of a Downhole Tool Measuring Real-Time Concentration of Ionic Tracers and pH in Geothermal Reservoirs Successful development of geothermal power plants is dependent on understanding reservoir properties such as the extent and interconnectivity of rock fractures. One method used to elucidate the fracture network between production and injection wells is to monitor the flow of tracers between the wells. FIG. 1 contains a notional diagram of how an injection well and a production well might be interconnected. Currently, tracer return curves are measured by collected samples from the wellhead manually. These samples are then sent to a laboratory, where the tracer concentration is measured by techniques such as inductively coupled plasma-mass spectrometry (ICP-MS), ICP-Optical Emission Spectroscopy (ICP-OEC), Ion Chromatography (IC), and High Performance Liquid Chromatography (HPLC) with fluorescence detection.

While these detection methods offer high sensitivity, they require a person to manually collect cooled samples from the wellhead and send them off-site for analysis. It may be days to weeks before the scientist conducting the tracer test receives the data. Perhaps more important however is the fact that the measured tracer concentration represents an average over the entire depth of the wellbore, which is often thousands of feet long. While this method provides information of tracer transit time through the reservoir, it does not provide information on the depth of the fractures that are connected to the injecting well.

Here, we describe a downhole tool capable of measuring the concentration of some ionic geothermal tracers, such as iodide, at depth in real-time. This will allow for the generation of tracer return curves with depth information. In addition, we will also be able to measure the pH of the fluid under actual temperature and pressure conditions. Because pH is highly dependent on the chemical species in solution, which in turn are dependent on temperature and pressure, it is difficult to accurately reconstruct what the actual pH at depth is based on samples that have been cooled and depressurized.

Iodide ions have been used in a number of geothermal tracer tests including studies in Iceland and Japan (Axelsson G et al., "Analysis of tracer test data, and injection-induced cooling, in the Laugaland geothermal field, N-Iceland," *Geothermics* 2001 December; 30(6):697-725; Kumagai N et al., "Characterization of geothermal fluid flows at Sumikawa geothermal area, Japan, using two types of tracers and an improved multi-path model," *Geothermics* 2004 June; 33(3):257-75). In the test conducted in Iceland, 45.3 kg was injected in one well, and samples were collected in production wells nearby. The authors of that study measured iodide tracer concentrations on the order of 10's ppm in production wells.

Sensors designed to operate inside geothermal wells must survive exceptionally harsh conditions. Typical geothermal wells can have temperatures ranging from 100° C.-350° C. and pressures in the 1,000's psi range. Wellbore depths are typically on the order of 1,000's of feet deep. The chemistry of the reservoir brine can vary widely depending on the local geology. For example, brine pH has been measured from 2 to 11, however a number of wells have pH values in the 5-8 range. The amount of total dissolved solids (TDS) can range from 1,000 ppm to up to 100,000 ppm in places, such as the Salton Sea area in southern California. Table 1 contains information on the surrogate brine we used to measure the ambient temperature behavior of our I-ISE. Our design goal for this new downhole tool was for successful operation up to 225° C. and 3000 psi.

TABLE 1

Surrogate brine chemistry used for ambient temperature I-ISE testing.

| Species | Concentration (mM) |
| --- | --- |
| $Na^+$ | 77.44 |
| $K^+$ | 5.57 |
| $Cl^-$ | 65.18 |
| $HCO_3^-$ | 17.83 |

Experimental

Tool Overview:

Our downhole geothermal tracer concentration and pH tool includes the following major components: a temperature sensor; a pressure sensor; a flow rate sensor; a ruggedized high temperature stable iodide ion selective electrode; a ruggedized high temperature stable reference electrode; and a ruggedized high temperature stable pH electrode.

Iodide Ion Selective Electrode (I-ISE):

We have designed a ruggedized version of an I-ISE that is able to survive the harsh environments found in typical geothermal wells. The I-ISE included an ion selective membrane (ISM), an electron conductor, the electrode tube body, and a high-pressure fitting.

Figure 4A:
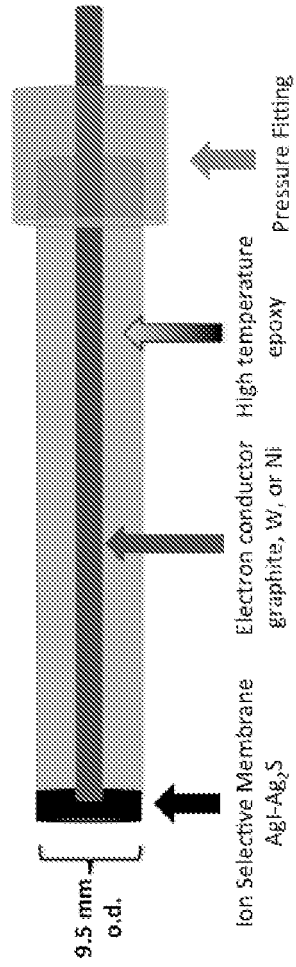
FIG. 4A-4B shows (A) a schematic drawing and (B) a line drawing of a ruggedized high temperature and pressure stable iodide ion selective electrode (I-ISE).
Figure 4B:
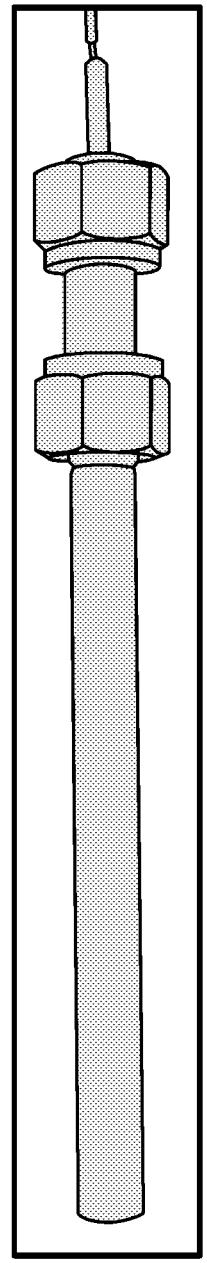

FIG. 4A-4B provides a schematic drawing and a line drawing of the I-ISE design used in this study. The ion selective membrane was a pellet containing silver iodide (AgI) and silver sulfide ($Ag_2S$) in various ratios. For example, for an ISM containing a 1:1 iodide to sulfur ratio, we mixed 0.250 g of AgI with 0.250 g of $Ag_2S$ using a mortar and pestle. The powder was then pressed at 1.8 metric tons using a hydraulic press. Next, the ISM pellet was fired at 375° C. in air for one hour. Iodide ISMs based on $AgI/Ag_2S$ mixtures have been demonstrated to have the sensitivity needed for this application, which is on the order of one ppm iodide (Rajbhandari N et al., "Characterization of home-made silver sulphide based iodide selective electrode," *Talanta* 2010 Sep. 15; 82(4):1448-54; Abdel-Latif M S et al., "A novel potentiometric solid-state iodide sensor," *Anal. Lett.* 2007 March; 40(4):729-36).

In order to better establish electrical connectivity to the ISM, a small hole was drilled to approximately ⅓ the thickness of the pellet. The electron conductor used in this study was a 3.2 mm diameter rod. The rod was bonded to the ISM using a high temperature conductive epoxy. The I-ISE body was constructed of stainless steel with an outer diameter of 9.5 mm and an inner diameter of 7.6 mm. The ISM pellet and rod were placed inside the steel tube and sealed using a high-temperature non-conductive epoxy.

High Temperature and Pressure Stable pH and Reference Electrodes:

High temperature and pressure stable pH and reference electrodes suitable for use in an autoclave were purchased from Con Instruments. The High Model A2 pH electrode is a solid-state design using a $ZrO_2$ membrane. The silver-silver chloride reference electrode was an internal pressure balanced design containing potassium chloride solution. These electrodes contain some parts that reside outside the autoclave and cannot be exposed to temperatures above 100° C. For this reason, the integrated apparatus can include one or more ruggedized pH and reference electrodes (e.g., any described herein) for use in the downhole environment, where the entire tool will be at 225° C.

Electrochemical Experiment Design:

For ambient and near-ambient testing, electrochemical measurements were determined using a Gamry Reference 3000 potentiostat. I-ISE response was established by measuring the open circuit potential difference between the I-ISE and a silver/silver chloride reference electrode produced by Radiometer.

High temperature and pressure experiments were conducted in a one liter autoclave. A HPLC pump (SSI Series 3) was used to deliver test solution to the autoclave. I-ISE measurements were conducted using 0.01 M potassium nitrate as the electrolyte. Iodide concentration was adjusted using the method of standard additions while under continuous stirring. The measurements used a NI-9234 16-bit analog to digital converter (ADC), which simultaneously monitored the potential of I-ISE, pH, and reference electrodes. The autoclave itself was ground, and all the potential measurements were referenced to it. The potential difference was obtained by subtracting the reference electrode potential for the I-ISE potential.

Figure 5:
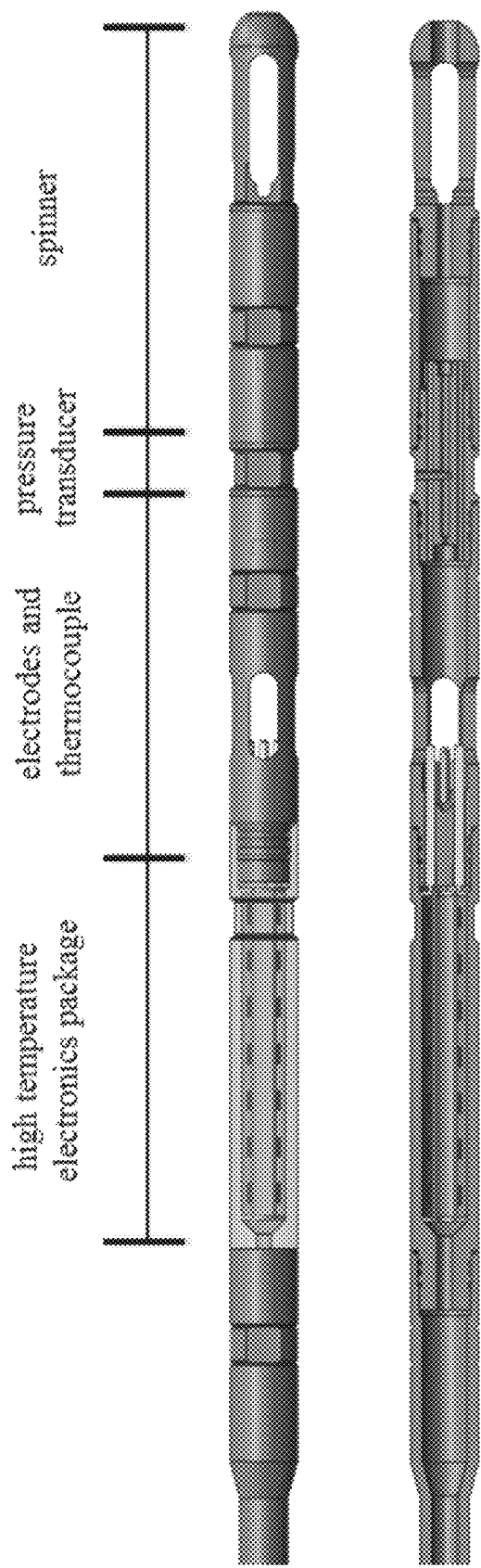
FIG. 5 shows a diagram of an exemplary downhole apparatus capable of measuring temperature, pressure, and flow rate. The ruggedized I-ISE, pH, and reference electrodes will be housed in the middle section.

Tool Construction:

The high-temperature tool will include four sections, where the proximal end can include a flow sensor (a spinner) and the distal end is configured to attach to a wireline. FIG. 5 shows these four sections (from left to right): a high temperature electronics package, a sensor section including three electrodes and a thermocouple, a pressure transducer section, and a flow sensor section.

The electronics section will house the electronic package. All the sensors will be connected to a HT 12-bit ADC via an HT analog multiplexer. For the electrodes, an additional analog stage can be included in order to shift the potentials into a range that can be recorded by the ADC. The ADC and the multiplexer will be controlled by the HT micro-processor. The micro-processor will communicate the recorded data via the single conductor (inter conductor and shield) logging wireline to the surface using PSK encoding.

The flow sensor section will house the spinner, which will be used as a flow sensor. To calculate the rotation speed of the spinner, the shaft of the spinner will have an integrated magnet that will open and close a reed switch.

Chemicals and Solutions:

The chemicals used in this study, including KI, KCl, NaCl, $KNO_3$, $NaHCO_3$, HCl, and NaOH, were of analytical grade. Solutions were made from distilled water.

Material Characterization:

$AgI/Ag_2S$ pellets were characterized by powder x-ray diffraction (PXRD) on a PANalytical X'Pert Pro diffractometer using CuKα radiation with a step size of 0.0167 degree and dwelling time of 0.152°/sec. Thermal properties characterization using thermogravimetric analysis (TGA) and differential scanning calorimetry (DSC) were carried out on a Mettler instrument. The material was heated to 1000° C. at a rate of 5° C./minute, and data were collected during both heating and cooling back to ambient temperature. PXRD was conducted to verify the presence of AgI and $Ag_2S$ in the ISM pellet. Thermal analysis was conducted to determine the temperature stability of the ISM pellet in air.

Iodide Ion Selective Electrode Performance

Figure 6:
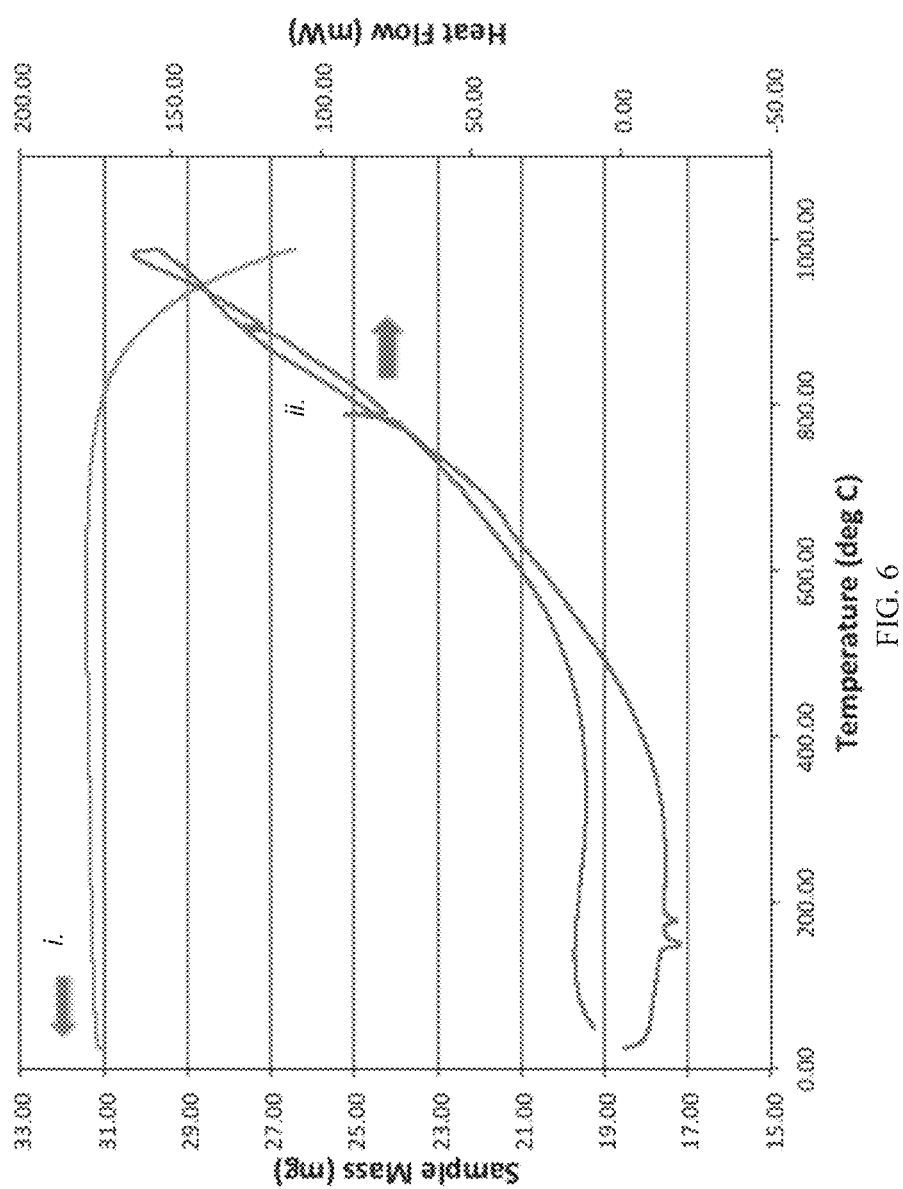
FIG. 6 is a graph showing thermal analysis of a 1:1 $AgI-Ag_2S$ mixture of an ion selective material (ISM) for iodide $I^-$. The primary y-axis contains Thermo Gravimetric Analysis (TGA) data (curve i), while the secondary y-axis contains Differential Scanning calorimetry (DSC) data (curve ii).

The iodide ion selective membranes used in this study included mixtures of AgI and $Ag_2S$ powders pressed into pellets with cylindrical geometries. Because our I-ISE must be able to withstand the high temperatures found in geothermal wells, the thermal stability of the ISM is critical to the electrode performance. FIG. 6 contains a plot of the TGA and DSC data collected on a mixture of AgI and $Ag_2S$ in a 1:1 ratio. These data show that there was no significant mass loss below 500° C. The DSC data showed two phase transitions at relatively low temperature: a first peak at 149° C. indicating the AgI beta to alpha phase transition and a second peak at 177° C. indicating the $Ag_2S$ alpha to beta phase transition.

In order to efficiently screen a number of different I-ISE designs, we conducted the majority of our experiments under ambient temperature and pressure conditions. We have also tested our I-ISEs under elevated temperature and pressure conditions in a laboratory-scale autoclave.

Figure 7:
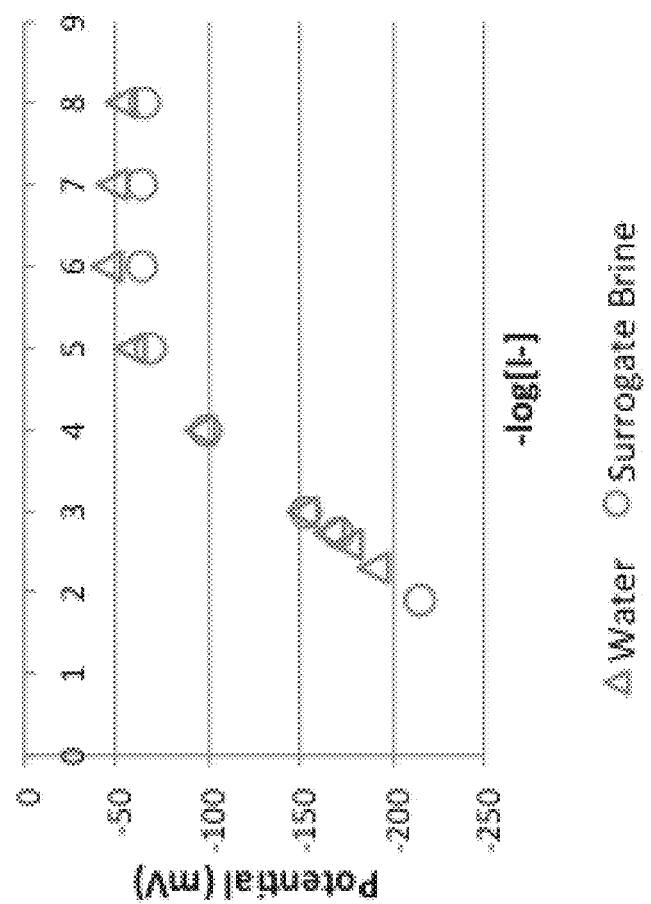
FIG. 7 is a graph showing I-ISE response in water (triangle) and in surrogate brine (circle). This electrode included a 1:1 $AgI-Ag_2S$ pellet as the ISM and a 1.5 mm diameter tungsten rod conductor in a Teflon® body. The I-ISE responded to changes in iodide concentration in a predictable manner in both water and the surrogate brine, which contained high amounts of chloride ion. For pI of 1 to 5, the slopes were 50 mV per decade iodide concentration for water ($R^2=0.994$) and 48 mV per decade iodide concentration for surrogate brine ($R^2=0.984$).

While other ratios of I:S were tested, we found the best results were obtained using a 1:1 ratio of AgI to $Ag_2S$. FIG. 7 shows the response found for an electrode using a 1:1 $AgI/Ag_2S$ ISM and a 1.5 mm outer diameter tungsten rod conductor potted inside a Teflon® outer tube using a UV-curable epoxy. We found that the electrode behaved almost identically in water and in surrogate brine. The surrogate brine used in this experiment had an ionic strength of 0.0830.

The slope of line generated from a plot of potential versus the log of the iodide concentration is a good diagnostic for the performance of an ISE. The theoretical value for the slope of an ISE response curve was 59.16 mV per decade change in ion concentration (FIG. 7). Little to no response was observed upon increasing the iodide concentration from zero through approximately $10^{-6}$ M. Between $10^{-6}$ M to $10^{-5}$ M, we observed a linear response to changing iodide concentration through $10^{-2}$ M iodide. The slope of this linear portion of the response curve was 50 mV/decade for iodide in distilled water ($R^2$=0.994). The slope for the same electrode in surrogate brine was 48 mV/decade ($R^2$=0.984). These responses are comparable to the theoretical value of 59.16 mV/decade, which indicates that the present system is a viable means of measuring iodide concentration at least under ambient conditions.

Because the slopes were so close in value between water and surrogate brine, we do not believe we will face significant interference issues in our systems of interest. However, as the fluid chemistry varies from well to well, further investigation of response in the presence of interferents can be performed. Our best limit of detection to data, as defined by the intersection of the flat portion and linear portions of the response curve, is on the order of one ppm iodide in surrogate brine under ambient conditions.

Figure 8:
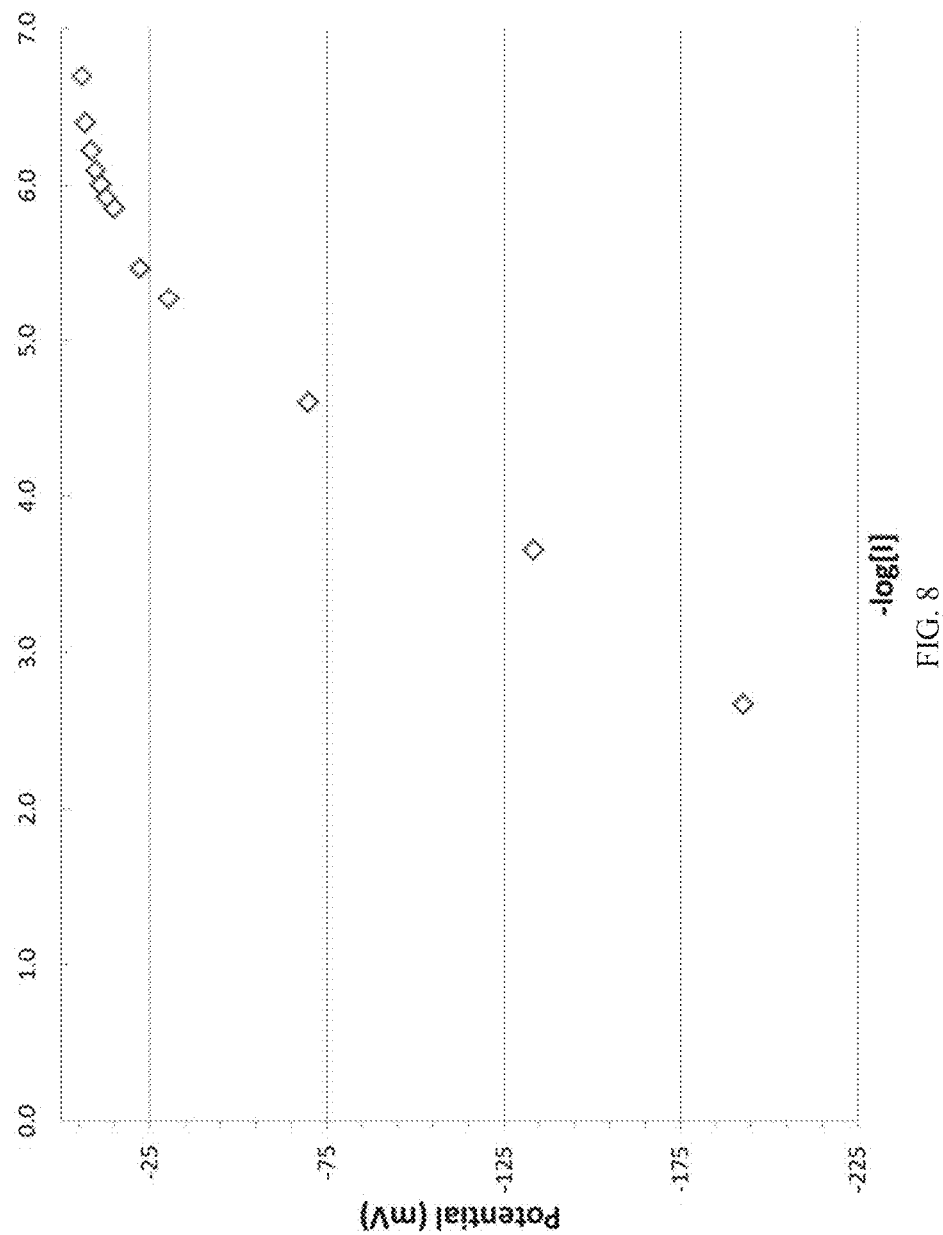
FIG. 8 is a graph showing the response of a ruggedized I-ISE at ambient temperature and pressure. The limit of detection was estimated at $3.4 \times 10^{-6}$ M iodide or a pI of 5.48. For pI of 2.67 to 5.48, the slope was 61 mV per decade iodide concentration ($R^2=0.998$).

While the Teflon® body design described above is easy to build and useful for screening ISM candidates, it is not very rugged. Our next generation design involved using the same ISM pellet composition and a 3.2 mm outer diameter nickel rod conductor potted inside a steel tube using high temperature stable conductive and non-conductive adhesives. The response of this ruggedized electrode design is shown in FIG. 8. From the linear portion of this plot, we calculated a slope of 61 mV/decade ($R^2$=0.998). We estimate the limit of detection to be 0.4 ppm iodide in surrogate brine under ambient conditions.

Figure 9:
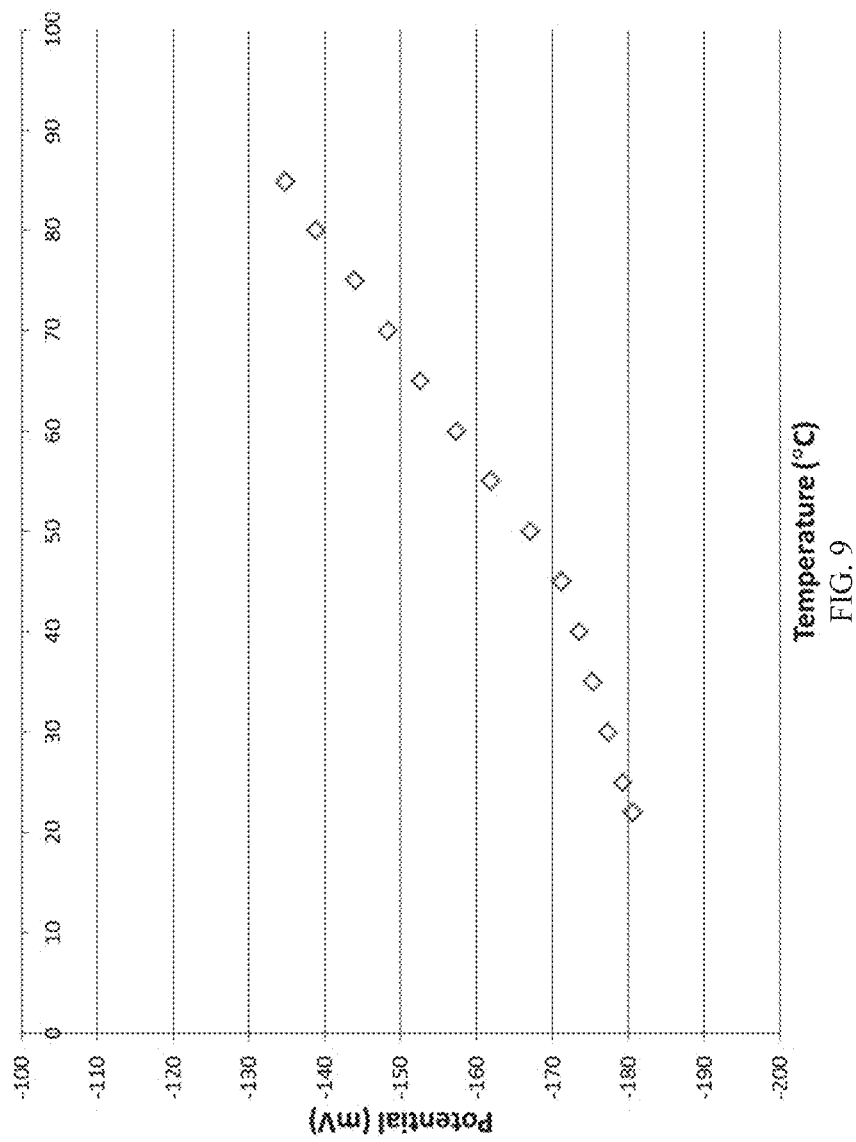
FIG. 9 is a graph showing the effect of temperature on an I-ISE including a 1:1 $AgI-Ag_2S$ ISM and a 3.2 mm diameter nickel conductor in a steel body. The potential increased by +44.6 mV over a 60° C. increase in temperature.

Prior to our autoclave experiments, we tested the performance of this electrode at elevated temperature, though still below the boiling point of water. FIG. 9 shows the change in potential with increasing temperature at a fixed iodide concentration in water of 0.001 M. We found that increasing the temperature from 25° C. to 85° C. resulted in an increase in potential of 44.6 mV (+0.74 mV/° C.).

Figure 10:
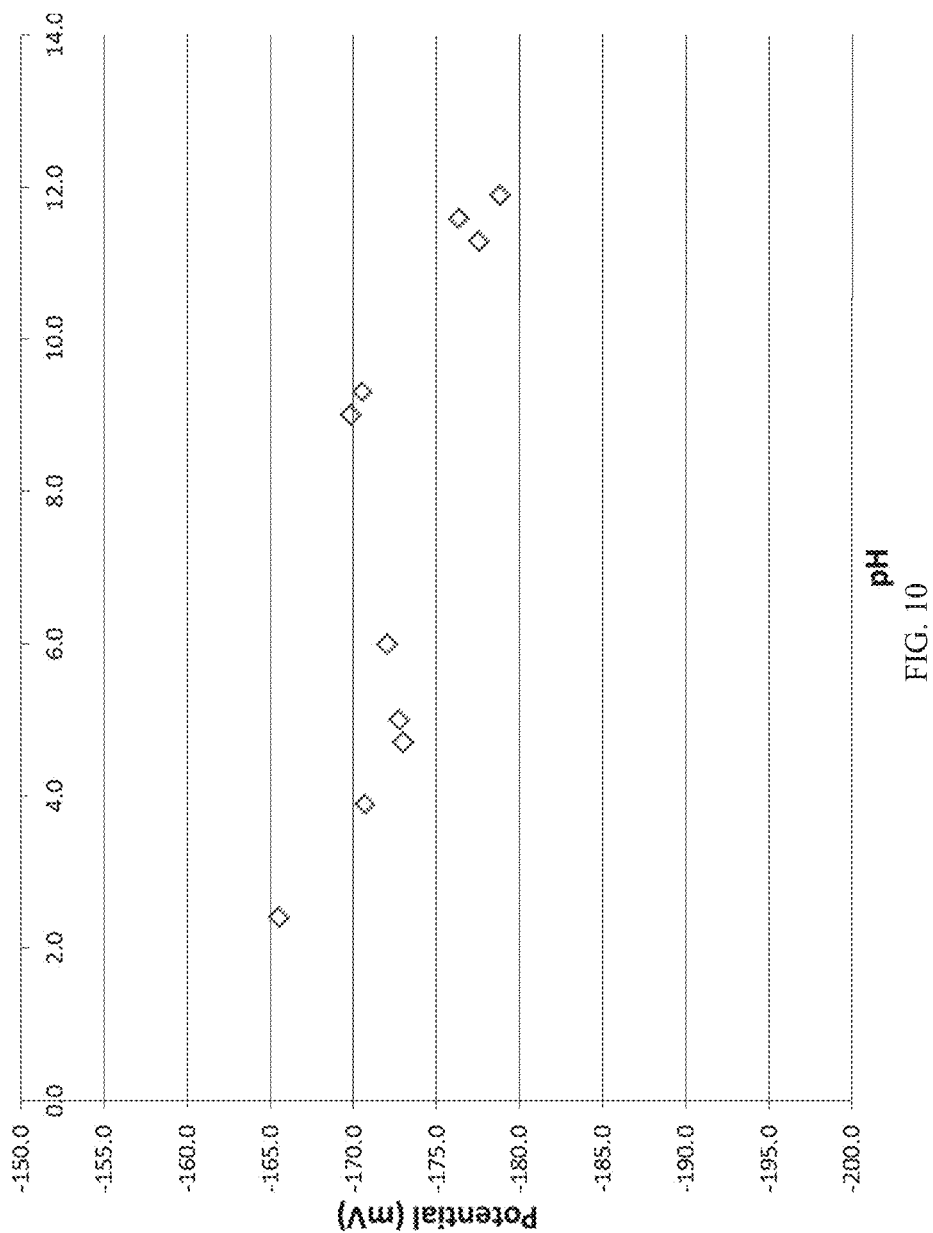
FIG. 10 is a graph showing the effect of pH on I-ISE response at a constant iodide concentration of 0.001 M in distilled water. These results indicate that this electrode design should work well in fluids with pH values in the 3-9 range.

Because the pH value of geothermal fluid varies greatly from location to location, it is important to determine the useful pH range for our ruggedized I-ISE. FIG. 10 shows potential versus pH at a fixed iodide in water concentration of 0.001 M at ambient temperature. From these data, we believe that this electrode design should work well for fluids with a pH between 3 to 9. Below and above this range, we observed that the potential begins to deviate significantly from that found around neutral pH, making calibration difficult.

High Temperature and Pressure Testing

Figure 11:
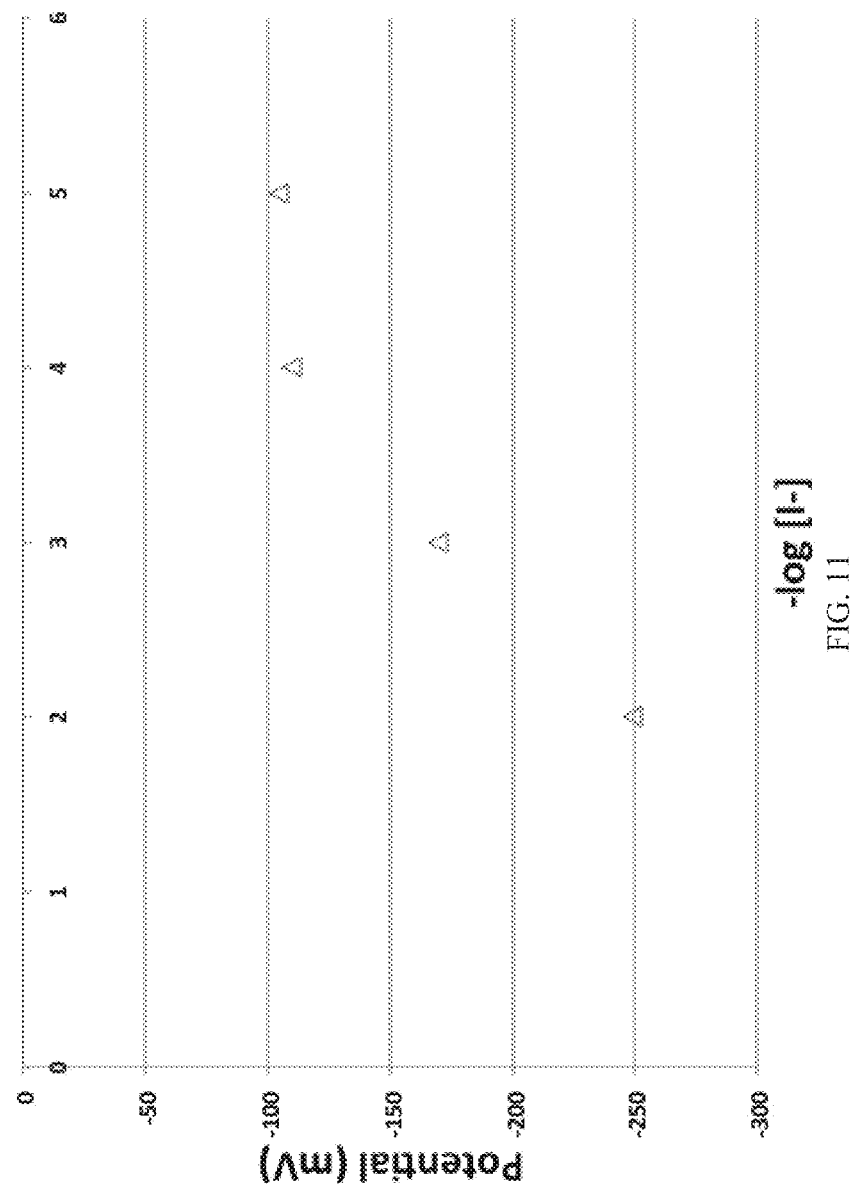
FIG. 11 is a graph showing I-ISE response at temperatures between 155° C. and 177° C. and pressures between 702 psi and 738 psi. A linear response was measured between $10^{-4}$ M and $10^{-2}$ M iodide with a slope of 70 mV per decade iodide concentration ($R^2=0.993$). The pH of the test solution was 6.

We also tested the ruggedized I-ISE designs at under elevated temperature and pressure conditions similar to those found in some geothermal wells. FIG. 11 shows the electrode response at temperatures ranging 155° C. to 177° C. with an average value of 161° C. The pressure in the autoclave ranged from 702 to 738 psi with an average value of 719 psi. The supporting electrolyte was 0.01 M potassium nitrate. Modifications to our autoclave and chemical delivery system are underway to increase the temperature and pressure stability during the course of the experiment.

This experiment shows that this I-ISE design has approximately Nernstian response for iodide concentrations in the $10^{-4}$ M to $10^{-2}$ M range with a slope of 70 mV/decade ($R^2$=0.993). The estimated limit of detection for this design was approximately 16 ppm.

Figure 12:
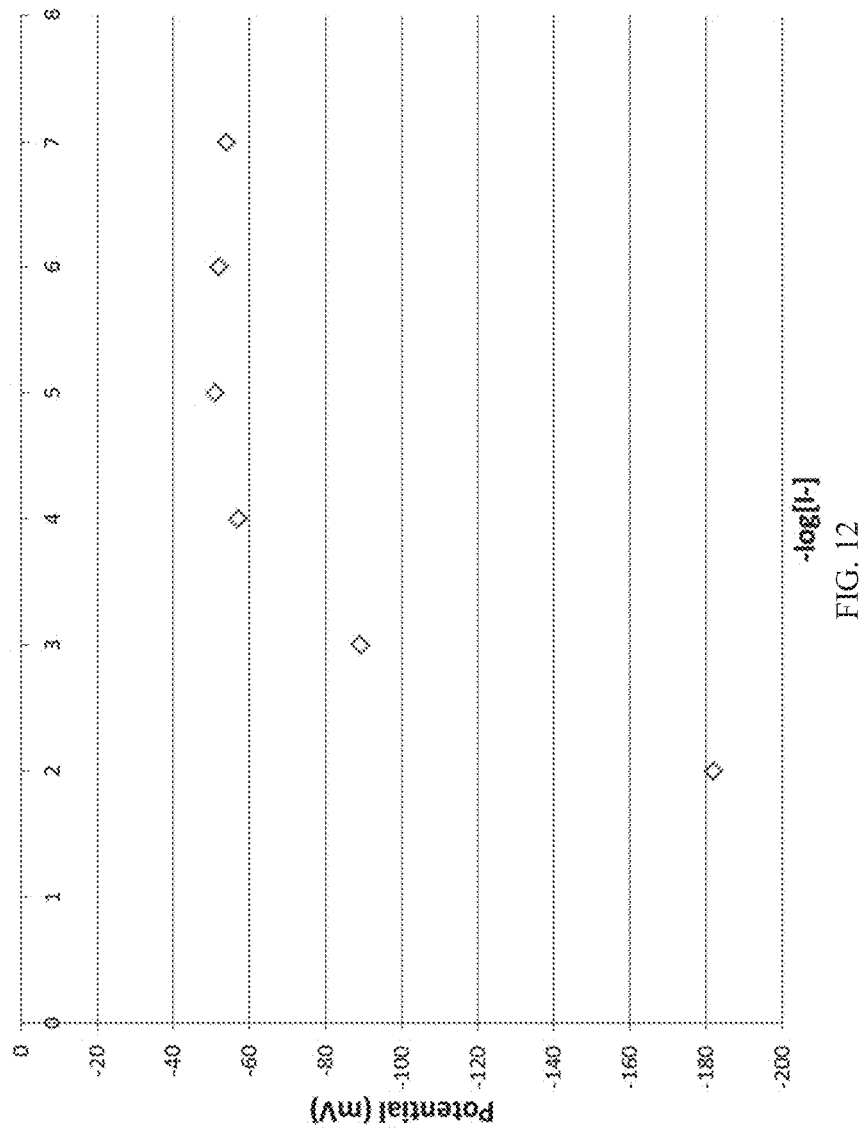
FIG. 12 is a graph showing I-ISE response at 200° C. and an average pressure of 1,171 psi. A linear response was measured between $10^{-4}$ M and $10^{-2}$ M iodide with a slope of 63 mV per decade iodide concentration ($R^2=0.926$). The pH of the test solution was 6.
Figure 13:
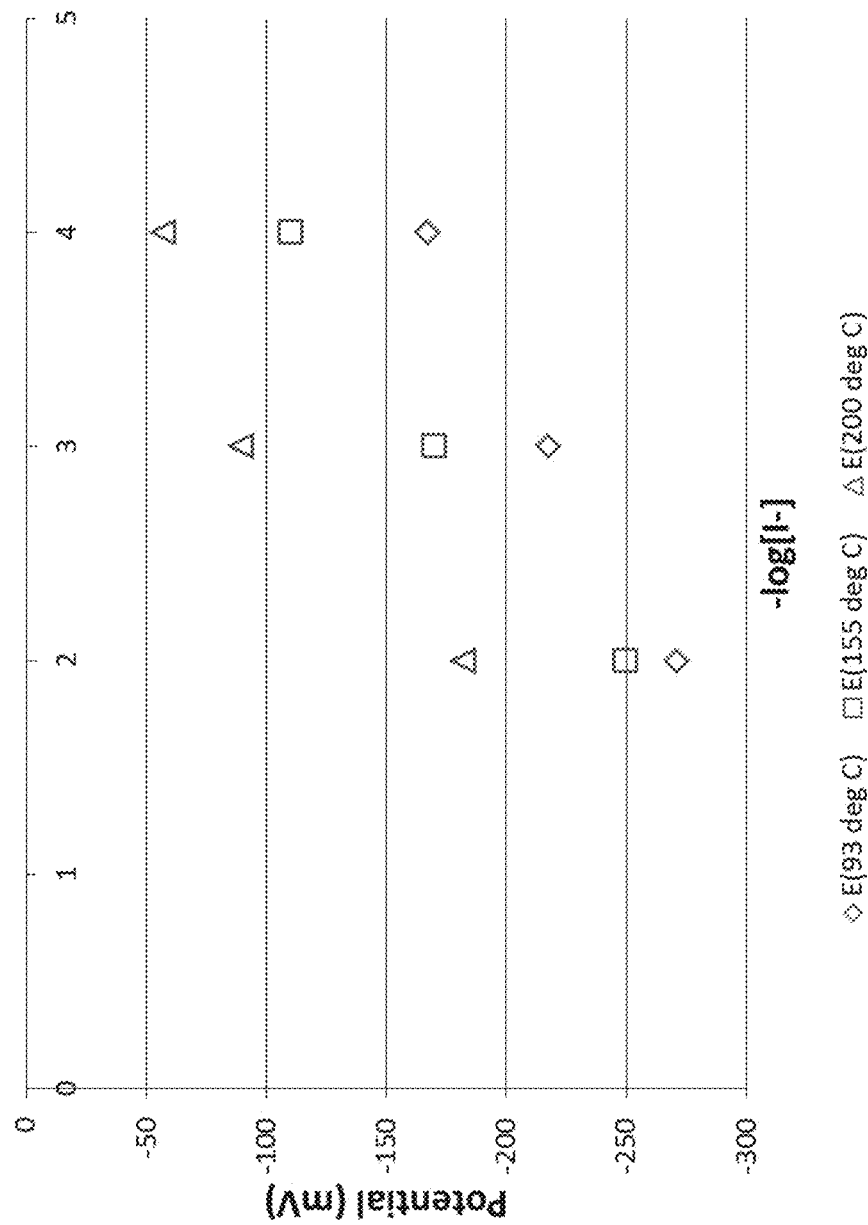
FIG. 13 is a graph showing I-ISE response as a function of iodide concentration and temperature. For a given iodide concentration, there is a positive increase in potential with increasing temperature, as expected from electrochemical theory.

We have tested this I-ISE design up to 200° C. with similar results. FIG. 12 shows the electrode response at 200° C. and an average pressure of 1,171 psi. The supporting electrolyte was 0.01 M potassium nitrate. At 200° C., we calculated a slope of 63 mV/decade ($R^2$=0.926) for iodide concentration in the $10^{-4}$ to $10^{-2}$ M range. FIG. 13 shows the linear portion of the I-ISE response at three different temperatures. As can be seen, there is a shift to less negative electrode potential as the temperature increases. These results show a stable response for the electrodes, which will allow us to detect changes in iodide tracer concentration under geothermal-relevant conditions.

Conclusions

We have developed a ruggedized iodide ion selective electrode for measuring changes in iodide concentration during geothermal reservoir tracer experiments. This electrode can be paired with ruggedized pH and reference electrodes (e.g., any described herein) and mounted on a wireline tool that already contains the capability to measure temperature, pressure, and flow rate in the harsh environments found in geothermal wells. Preliminary testing of our I-ISE design showed near Nernstian response for iodide concentrations in the $10^{-4}$ M to $10^{-2}$ M range at temperatures from 100° C. to 200° C. At 200° C., the estimated limit of detection was 16 ppm. Below 100° C., the linear response range was extended, and we calculated an estimated limit of detection of 0.4 ppm iodide. Efforts are underway to lower the limit of detection for our I-ISE design at elevated temperature and pressure (e.g., by employing any design consideration described herein).

Example 2: Development of a Ruggedized Cs-ISE to Monitor Cesium Ion Concentration We also developed and tested an ISE for detecting a $Cs^+$ tracer ion (Cs-ISE). The ISM for the Cs-ISE included $Cs_3Mo_{12}PO_{40}$ (Cs-MPO) or a thin disk membrane including Cs-MPO. The membrane was formed in a reaction including 350 mg of dibutylphthalate, 190 mg of poly(vinyl chloride), and 10 mg of $Cs_3Mo_{12}PO_{40}$ in tetrahydrofuran. Membranes can be formed by casting or dip-coating a rod.

Figure 14A:
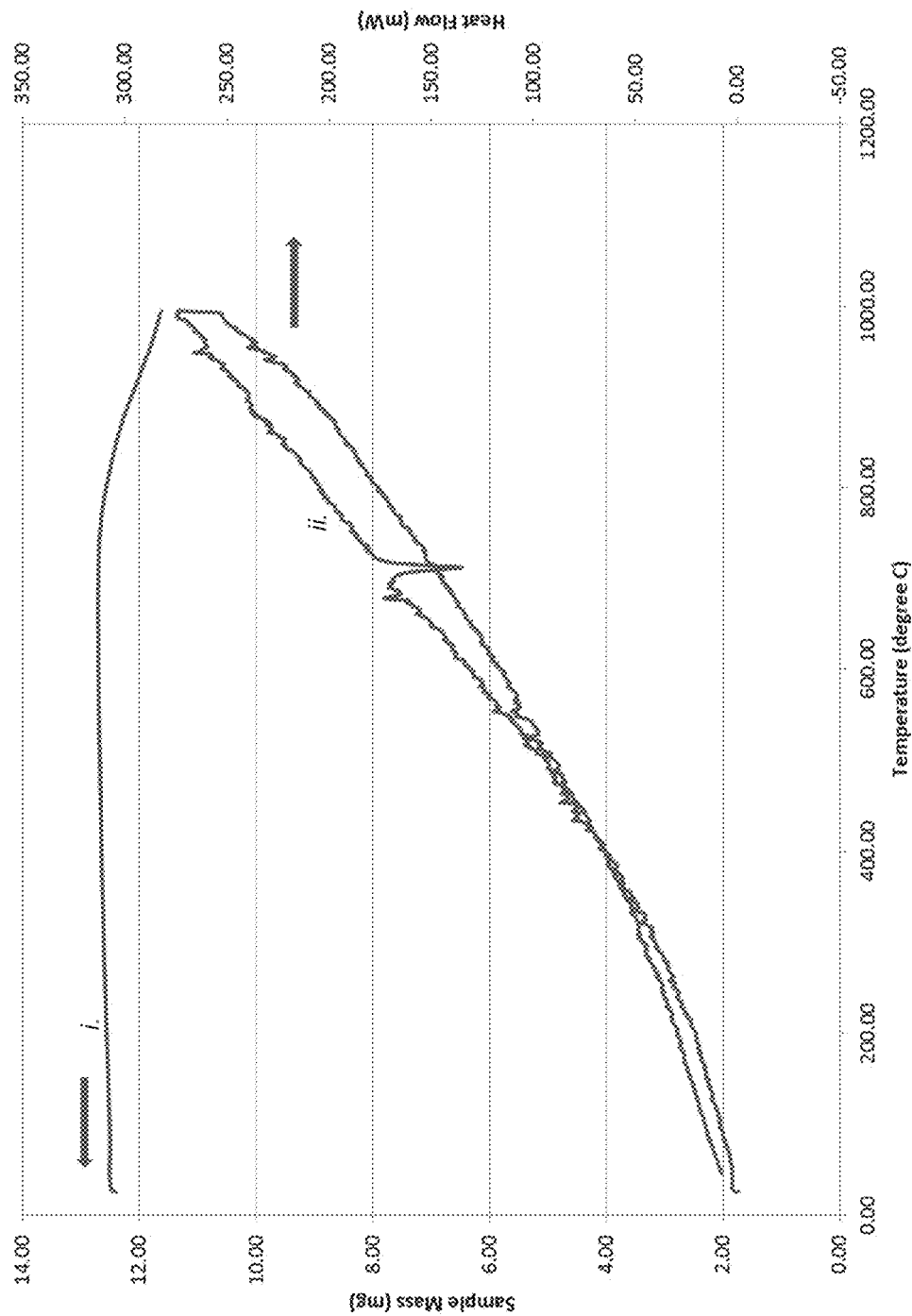
FIG. 14A-14B shows thermal analysis of cesium 12-molybdophosphate ($Cs_3Mo_{12}PO_{40}$), an ion selective material (ISM) for cesium $Cs^+$. Provided are graphs for (A) nominal cesium 12-molybdophosphate and (B) a dibutylphthalate-PVC membrane including cesium 12-molybdophosphate. The primary y-axis contains Thermo Gravimetric Analysis (TGA) data (curve i), while the secondary y-axis contains Differential Scanning calorimetry (DSC) data (curve ii).
Figure 14B:
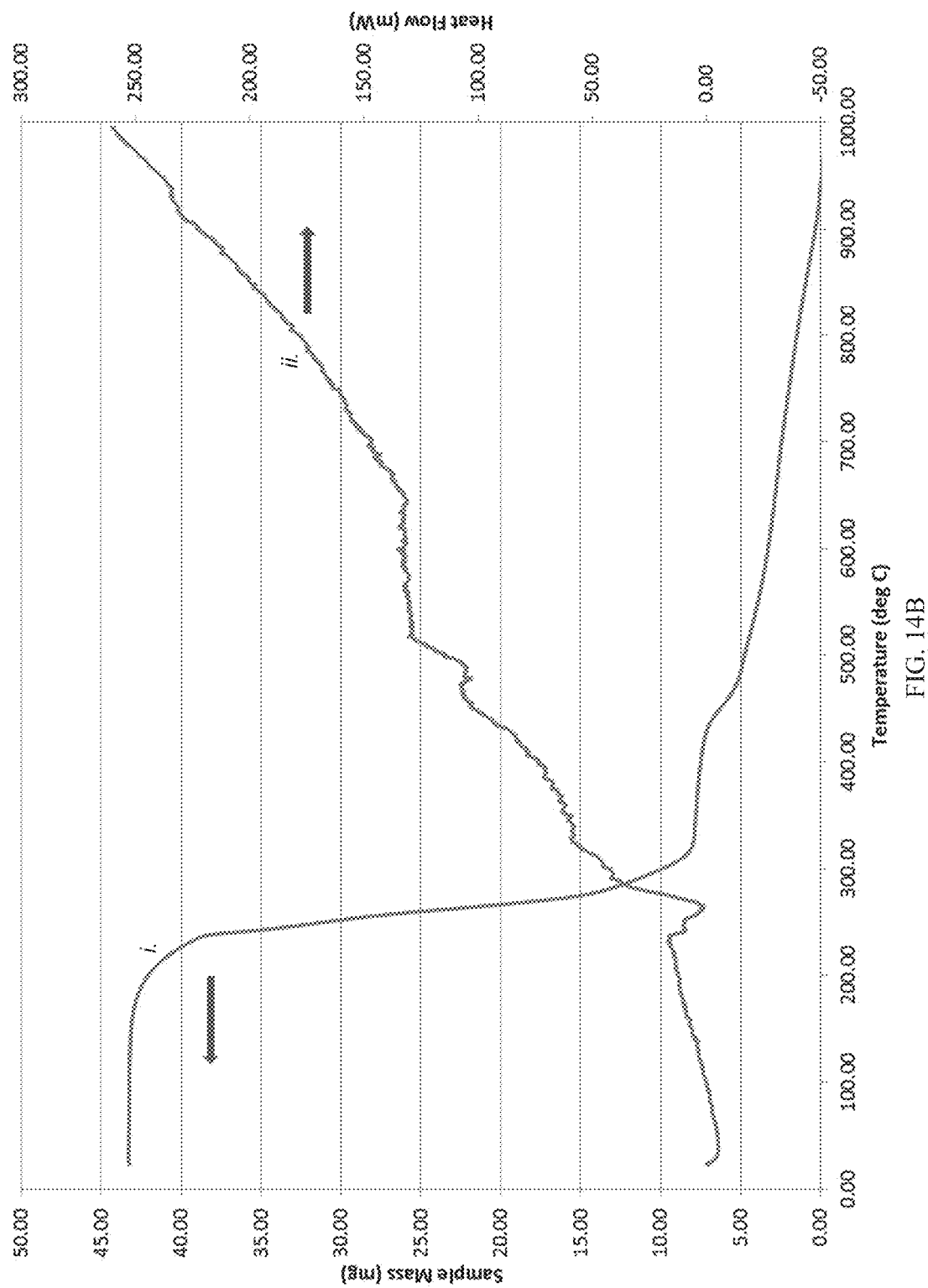
Figure 15A:
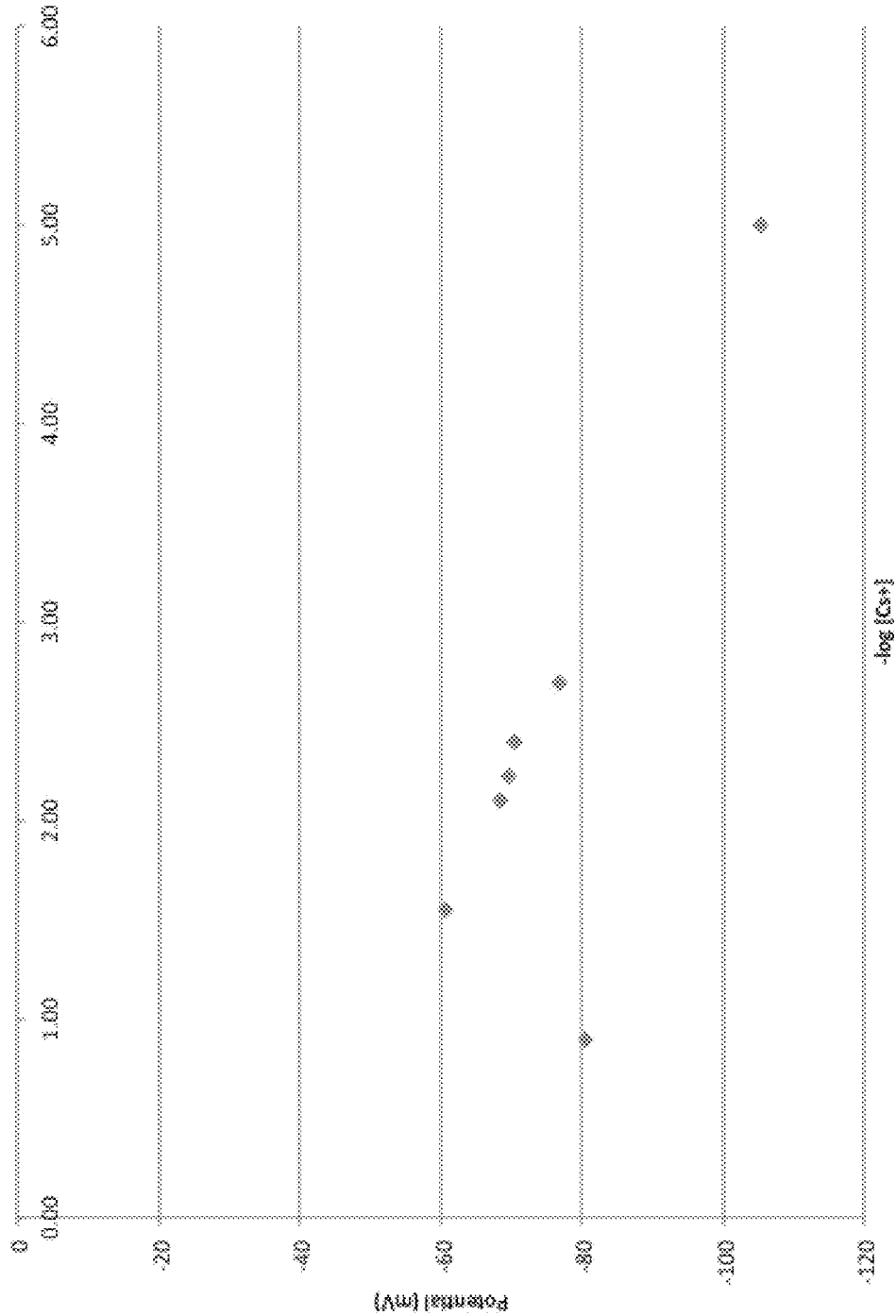
FIG. 15A-15B shows the response of a solid state cesium ion selective electrode (Cs-ISE) in water at different concentration ranges. This electrode included a dibutylphthalate-PVC membrane having cesium 12-molybdophosphate as the ISM and a graphite or tungsten rod conductor in a Teflon® body, which was connected via nickel wires.
Figure 15B:
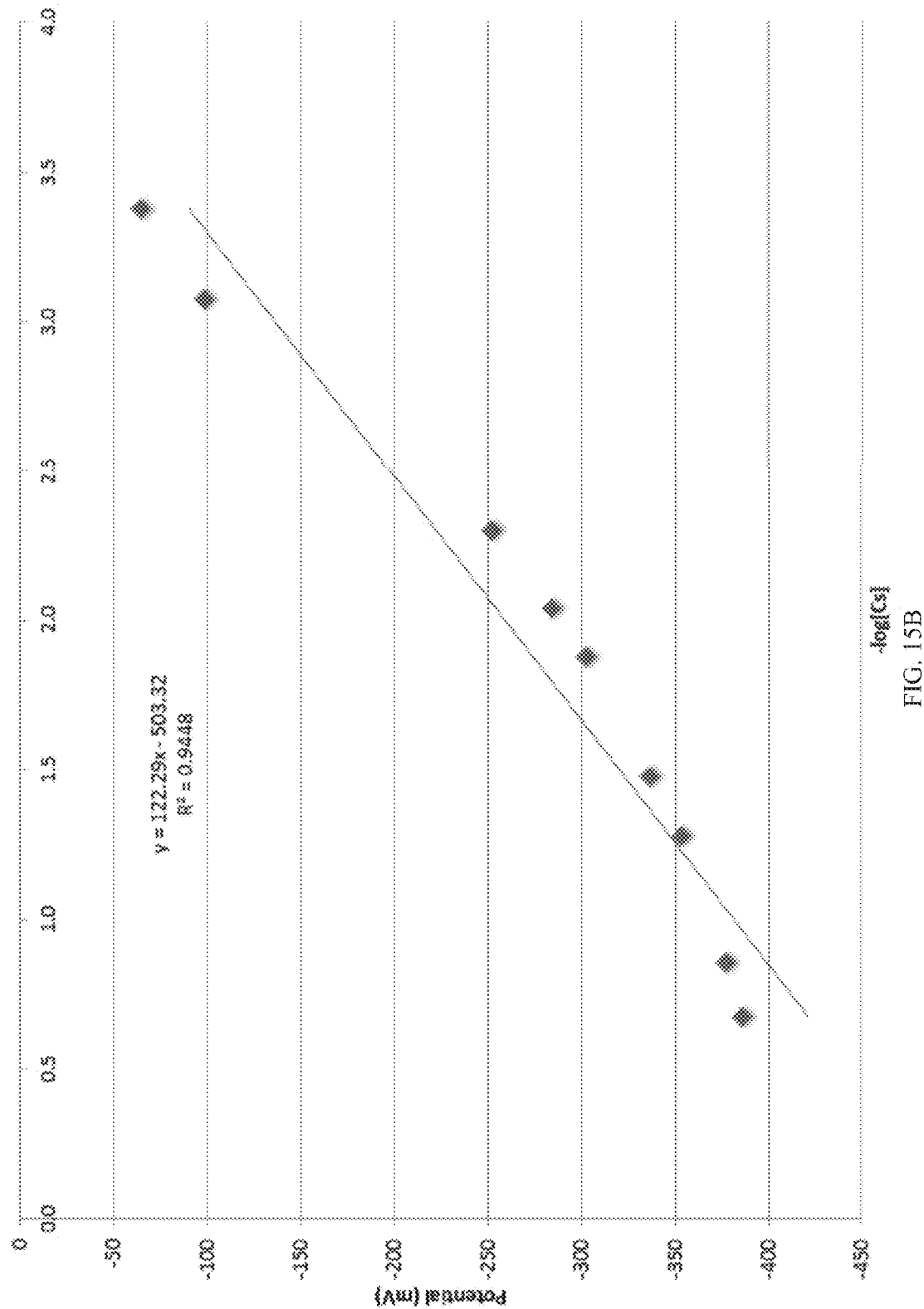

The thermal properties of Cs-MPO and the Cs-MPO membrane were characterized. As can be seen, FIG. 14A shows that $Cs_3Mo_{12}PO_{40}$ was stable to more than 225° C. As seen in FIG. 14B, the Cs-MPO membrane was stable to about 150° C. Preliminary data for ruggedized Cs-ISEs in water are provided in FIG. 15A-15B. As can be seen, the Cs-ISE provides a favorable response in water. Additional experiments can be conducted at high temperature and/or pressure conditions.

Example 3: Reference Probe

Ruggedized reference probes were also developed and tested. Given the high temperature and pressure conditions in a geothermal well, liquid-based electrode were avoided.

Figure 17:
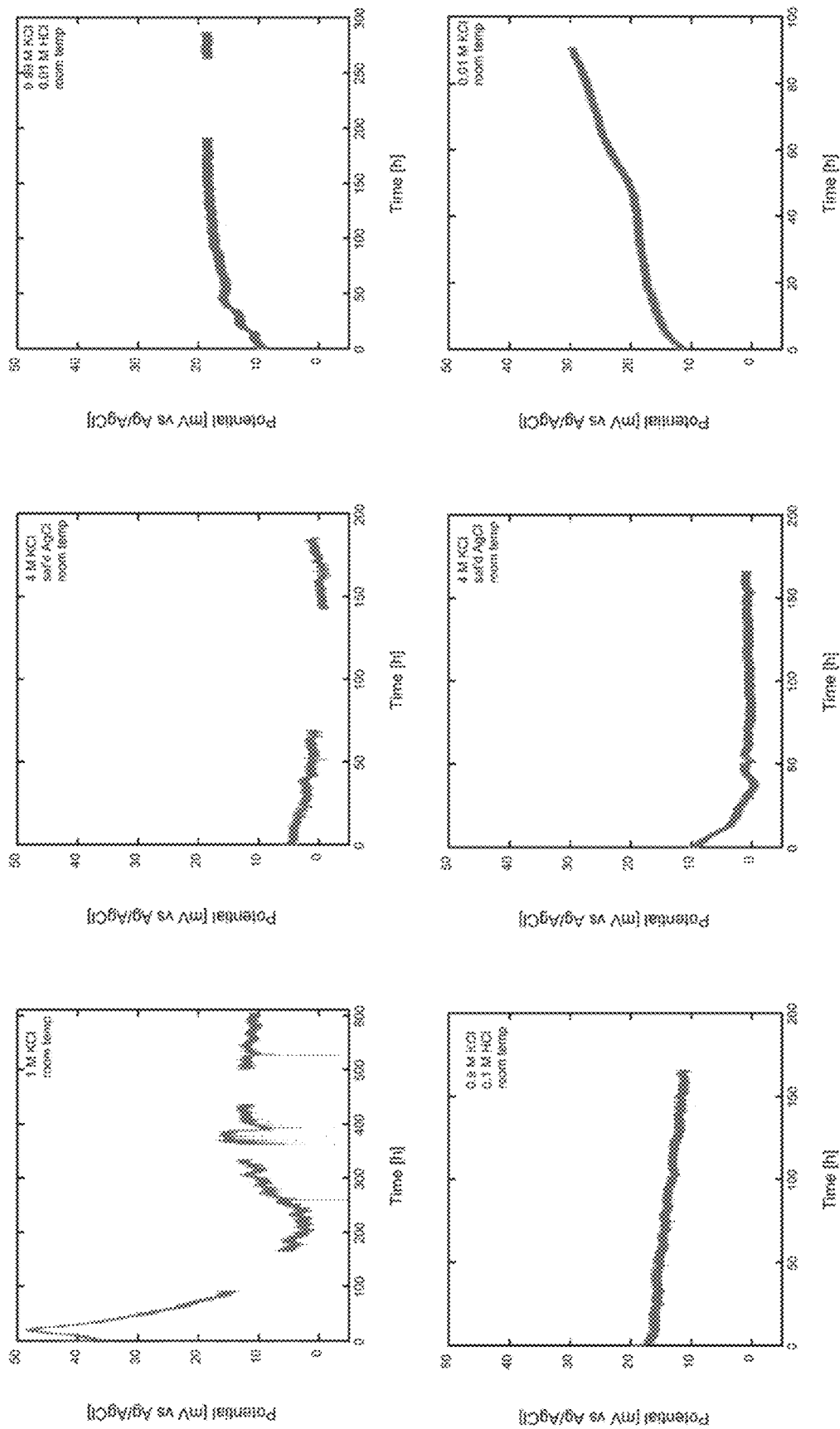
FIG. 17 shows graphs of reference electrode data obtained under various conditions. These graphs show the measured potential difference between the reference electrode and a commercial Ag/AgCl reference electrode in a variety of different solutions. As can be seen, after an initial break-in period, the electrode voltage is relatively stable over time, although the response does vary slightly with pH and chloride ion concentration.

For testing purposes, the reference probe included a Teflon® outer electrode body, an Ag/AgCl electron conductor, a frit disposed at the proximal end, and a potting material including a ceramic (alumina) set with KCl solution (FIG. 16). Preliminary data are provided in FIG. 17, and additional experiments can be conducted at high temperature and/or pressure conditions.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. An integrated downhole apparatus for measurements in high temperature and high pressure conditions, the apparatus comprising:
    a ruggedized ion selective electrode for high temperature and high pressure conditions, the ion selective electrode comprising:
        an electrode body comprising a temperature-resistant material, wherein the electrode body comprises an inner volume, a proximal end, and a distal end;
        a pressure fitting cap disposed at the distal end of the electrode body;
        an ion selective material disposed at the proximal end of the electrode body;
        an electron conductor disposed within the electrode body and connected electrically to the ion selective material, wherein the electron conductor comprises a conductive material that extends along at least a portion of an axial length of the electrode body; and
        a potting material comprising a solid, non-conductive material disposed within the electrode body, wherein the potting material conforms to fill the inner volume confined by a surface of the ion selective material and a surface of the pressure fitting cap;
    a ruggedized reference electrode comprising an electrode body, an electron conductor disposed within the electrode body, a frit disposed at a proximal end of the electrode body, and a potting material disposed within the electrode body, wherein the potting material conforms to fill an inner volume of the electrode body and comprises an electrolyte;
    a ruggedized pH electrode comprising a ceramic electrode body, an electron conductor disposed within the electrode body, and a metal material disposed within the electrode body, wherein the metal material conforms to fill an inner volume of the ceramic electrode body; and
    an electronic module comprising an analog multiplexer configured to receive the one or more potential measurements and to output an analog measurement signal, an analog-to-digital converter (ADC) configured to receive the analog measurement signal and to output a digital measurement signal, and a microprocessor configured to control the analog multiplexer and the ADC and to output an encoded signal to a logging wireline.

2. The apparatus of claim 1, wherein the potting material comprises an epoxy.

3. The apparatus of claim 1, wherein the ion selective material comprises a ceramic, a membrane, a crystal, or a pellet.

4. The apparatus of claim 3, wherein the ion selective material comprises a recessed portion configured to receive a proximal end of the electron conductor.

5. The apparatus of claim 4, further comprising a conductive adhesive disposed within the recessed portion and between the ion selective material and the electron conductor.

6. The apparatus of claim 1, wherein the electrode body comprises a temperature-resistant polymer, ceramic, metal, or a combination thereof.

7. The apparatus of claim 1, further comprising a lead wire electrically connected to the electron conductor.

8. The apparatus of claim 1, wherein the electronic module comprises:
  a high temperature level shifter configured to receive one or more signals from the ion selective electrode, reference electrode, and/or pH electrode and to transmit one or more shifted signals;
  an analog multiplexer configured to receive the one or more shifted signals from the level shifter and to transmit one or more multiplexed analog signals;
  an analog-to-digital converter configured to receive the one or more multiplexed analog signals and to transmit one or more digital signals; and
  a microprocessor configured to receive the one or more digital signals and to transmit the one or more digital signals to a receiver.

9. The apparatus of claim 1, further comprising a thermocouple, a pressure sensor, and/or a flow sensor.

10. The apparatus of claim 1, wherein the electronic module comprises a high temperature level shifter circuit configured to receive one or more electronic signals from the ion selective electrode, reference electrode, and/or pH electrode and to provide one or more shifted electronic signals.

11. The apparatus of claim 10, wherein the high temperature level shifter circuit comprises:
  a driver circuit configured to generate a square wave signal;
  an inverter circuit configured to receive the square wave signal and generate a negative voltage signal;
  an operational amplifier buffer circuit configured to receive the negative voltage signal and comprising an input configured to receive the one or more potential measurements from the ion selective electrode, reference electrode, and/or pH electrode, thereby providing one or more buffered output signals; and
  a summing circuit configured to receive the one or more buffered output signals and to generate one or more shifted signals.

12. The apparatus of claim 8, wherein the receiver is located uphole of the ion selective electrode.

13. The apparatus of claim 1, wherein the ion selective electrode comprises the conductive material that extends along an entire axial length of the electrode body.

14. The apparatus of claim 1, wherein the potting material of the ion selective electrode conforms to fill an entire inner volume confined by the surface of the ion selective material and the surface of the pressure fitting cap.

15. The apparatus of claim 1, wherein the reference electrode comprises the electron conductor comprising a conductive material that extends along at least a portion of an axial length of the electrode body.

16. The apparatus of claim 15, wherein the reference electrode comprises the conductive material that extends along an entire axial length of the electrode body.

17. The apparatus of claim 1, wherein the potting material of the reference electrode conforms to fill an entire inner volume of the electrode body.

18. The apparatus of claim 1, wherein the metal material of the pH electrode conforms to fill an entire inner volume of the ceramic electrode body.

19. The apparatus of claim 1, wherein the ion selective material comprises an iodide-selective material.

20. The apparatus of claim 1, wherein the temperature-resistant material is stainless steel or a polyether.

* * * * *